US007960571B2

(12) United States Patent
Nakao et al.

(10) Patent No.: US 7,960,571 B2
(45) Date of Patent: Jun. 14, 2011

(54) SILICON-BASED CROSS-COUPLING REAGENT AND PRODUCTION METHOD OF ORGANIC COMPOUND USING THE SAME

(75) Inventors: Yoshiaki Nakao, Kyoto (JP); Tamejiro Hiyama, Kyoto (JP)

(73) Assignee: Kyoto University, Kyoto-shi (JP)

( * ) Notice: Subject to any disclaimer, the term of this patent is extended or adjusted under 35 U.S.C. 154(b) by 858 days.

(21) Appl. No.: 11/918,261

(22) PCT Filed: Nov. 21, 2005

(86) PCT No.: PCT/JP2005/021382
§ 371 (c)(1),
(2), (4) Date: Oct. 11, 2007

(87) PCT Pub. No.: WO2006/112073
PCT Pub. Date: Oct. 26, 2006

(65) Prior Publication Data
US 2009/0069577 A1    Mar. 12, 2009

(30) Foreign Application Priority Data
Apr. 14, 2005   (JP) ................................. 2005-117452

(51) Int. Cl.
C07D 333/10  (2006.01)
(52) U.S. Cl. ............................................................ 549/4
(58) Field of Classification Search ........................ 549/4
See application file for complete search history.

(56) References Cited

FOREIGN PATENT DOCUMENTS
JP    04-283521    10/1992
JP    08-310972    11/1996

OTHER PUBLICATIONS

Gschwend et al., Org. Reactions, (1979), vol. 26.*
Rabideau et al., Org. Reactions, (1992), vol. 42.*
Fleming et al., Org. Reactions, (1989), vol. 37.*
Rickborn, Org. Reactions, (1998), vol. 53;.*
Beck, e-EROS Encyclopedia of Reagents for Org. Synthes. (2001).*
Comins et al., e-EROS Encyclopedia of Reagents for Org. Synthes. (2001).*
Campbell et al., e-EROS Encyclopedia of Reagents for Org. Synthes. (2001).*
Mathieu-Pelta, et al., e-EROS Encyclopedia of Reagents for Org. Synthes. (2001).*
Sorgi, et al., e-EROS Encyclopedia of Reagents for Org. Synthes. (2001).*
Ovaska, e-EROS Encyclopedia of Reagents for Org. Synthes. (2001).*
Haruhiko Taguchi et al. "Copper(I) *tert*-butoxide-promoted coupling of *o*-(1-hydroxyalkyl)arylsilanes with organic halides." Tetrahedron Letters 45, 2004, pp. 429-432.
Scott E. Denmark et al. "Organosilicon Compounds in Cross-Coupling Reactions." Metal Catalyzed Cross-Coupling Reactions, 2nd Edition, 2004 Wiley-VCH Verlag GmbH & Co. KgaA, Weinheim, pp. 163-216.

Kenichiro ITAMI et al. "A General and Straightforward Route toward Diarylmethanes. Integrated Cross-Coupling Reactions Using (2-Pyridyl)silylmethylstannane as an Air-Stable, Storable, and Versatile Coupling Platform." Organic Letters 2002, vol. 4, No. 21, Sep. 19, 2002, pp. 3635-3638.
James C. Anderson et al. "Vinyldimethylphenylsilanes as Safety Catch Silanols in Fluoride-Free Palladium-Catalyzed Cross-Coupling Reactions." J. Org. Chem. 2004, Nov. 9, 2004, pp. 8971-8974.
Emiko Hagiwara et al. "NaOH-Promoted Cross-Coupling Reactions of Organosilicon Compounds with Organic Halides: Practical Routes to Biaryls, Alkenylarenes and Conjugated Dienes." Tetrahedron Letters, vol. 38, No. 3, 1997, pp. 439-442.
Christian Wolf et al. "Palladium-Phosphinous Acid-Catalyzed NaOH-Promoted Cross-Coupling Reactions of Arylsiloxanes with Aryl Chlorides and Bromides in Water." Organic Letters 2004, vol. 6, No. 7, Mar. 9, 2004, pp. 1147-1150.
Kazunori Hirabayashi et al. "Palladium-Catalyzed Cross-Coupling of Silanols, Silanediols, and Silanetriols Promoted by Silver(I) Oxide." J. Org. Chem. 2000, Jul. 29, 2000, pp. 5342-5349.
Haruhiko Taguchi et al. "Copper(I) tert-Butoxide-Promoted 1,4 $C^{sp^2}$toO Silyl Migration: Generation of Vinyl Copper Equivalents and Their Stereospecific Cross-Coupling with Allylic, Aryl, and Vinylic Halides." J. Org. Chem. 2002, Nov. 1, 2002, pp. 8450-8456.
Mitsuru Shindo et al. "Intramolecularly Activated Vinylsilanes: Fluoride-Free Cross-Coupling of (Z)-β-(Trialkylsilyl)acrylic Acids." Synlett 2005, No. 1, pp. 0176-0178.
Akira Hosomi et al. "Pentacoordinate Organosilicon Compounds in Organic Synthesis: Cross-Coupling of Alkenylsiliconates with Organic Halides and Triflates Catalyzed by Palladium Complex." Chem. Pharm. Bull, 1988, pp. 4622-4625.
W. Michael Seganish et al. "Palladium-Catalyzed Cross-Coupling of Aryl Triethylammonium Bis(catechol) Silicates with Aryl Bromides Using Microwave Irradiation." Organic Letters 2004, vol. 6, No. 23, Oct. 22, 2004, pp. 4379-4381.
Paul F. Hudrlik et al. "Alkoxides of *o*-silyl benzyl alcohols in cleavage reactions: approaches to benzyl and silyl anion equivalents." Can. J. Chem., Oct. 25, 2000, pp. 1421-1427.
Paul F. Hudrlik et al. "Generation of Anionic Intermediates by Intramolecular Nucleophilic Attack at Silicon." Tetrahedron Letters, vol. 33, No. 45, 1992, pp. 6747-6750.
Yohsuke Yamamoto et al. "Intramolecular Cyclization of *o*-Silylbenzyl Alcohols with Elimination of Hydrocarbon Via Hypervalent Silicon Intermediates: Effect of Structure on the Selectivity for Elimination." Tetrahedron Letters, vol. 30, No. 6, 1989, pp. 725-728.
John W. Fitch et al. "Lithiation and silylation reactions of 1,4-bis(1,1,1,3,3,3-hexafluoro-2-hydroxy-2-propyl) benzene." Journal of Organometallic Chemistry 522, 1996, pp. 55-57.

(Continued)

*Primary Examiner* — Taofiq A Solola
(74) *Attorney, Agent, or Firm* — Harness, Dickey & Pierce, P.L.C.

(57) ABSTRACT

In one embodiment of the present invention, a silicon-based cross-coupling reagent is disclosed which is a highly stable tetraorganosilicon compound allowing for a cross-coupling reaction under mild reaction conditions without using fluoride ions, transition metal promoter, or strong bases, and the residue of the silicon reagent can be recovered and reused. The silicon-based cross-coupling reagent is a silicon compound in which an o-hydroxymethylphenyl group is connected to a silicon atom for intramolecular activation.

6 Claims, No Drawings

OTHER PUBLICATIONS

Ulrich Wannagat et al. "Beiträge zur Chemie der Silicium-Stickstoffverbindungen." Journal of Organocmetallic Chemistry, 1988, pp. 95-108. English Abstract.

Shaundra Riggleman et al. "Application of Silicon-Based Cross-Coupling Technology to Triflates." J. Org. Chem. 2003, Sep. 25, 2003, pp. 8106-8109.

Yousef M. Hijji et al., "Preparation of o-(Silyl) Benzyl Alcohols", Synthetic Communications, 27 (24), 4297-4308 (1997).

"Silicon-based Cross-Coupling Reaction via Intramolecular Activation": The Chemical Society of Japan, 85th Spring Meeting 2005, Lecture Proceedings II, p. 909 4 A6-09 (Mar. 11, 2005).

"Fluoride-free Silicon-based Cross-Coupling Reaction via Intramolecular Activation": The 4th International Symposium of the Kyoto COE Project, Elements Science, p. 122, Jan. 6, 2005.

* cited by examiner

SILICON-BASED CROSS-COUPLING REAGENT AND PRODUCTION METHOD OF ORGANIC COMPOUND USING THE SAME

TECHNICAL FIELD

The present invention relates to a silicon-based cross-coupling reagent and a production method of an organic compound using the same. Particularly, the present invention relates to (i) a highly stable silicon-based cross-coupling reagent which allows for a cross-coupling reaction under mild conditions and reuse of a residue of the reagents, and (ii) a production method of an organic compound using the silicon-based cross-coupling reagent.

BACKGROUND ART

A cross-coupling reaction is an extremely important synthetic reaction which allows for direct formation of a bond between $sp^2$ carbons or the like. In the cross-coupling reaction, an aryl halide or an alkenyl halide in which a halogen atom is connected to an $sp^2$ carbon of aromatic series or olefin is reacted with an organo metallic compound or acetylene in the presence of a transition metal catalyst such as nickel and palladium. As the result, the halogen atom connected to the $sp^2$ carbon of aromatic series or olefin is substituted by the organic group. Hence, the cross-coupling reaction is essential in constituting n-conjugated systems serving as key compounds of medicinal intermediates or molecular-scale electronics elements.

As the organometallic reagents used in the cross-coupling reaction, there are various kinds of organo metallic compounds, such as organo magnesium, zinc, boron, silicon, tin, or the like. Above all, currently, boron-based cross-coupling reagents in which boron is connected to $sp^2$ carbon are most widely used due to its stability and excellent selectivity of cross-coupling reaction. Dozens of kinds of such boron-based cross-coupling reagents come onto the market from chemical producers such as TOKYO CHEMICAL INDUSTRY CO., LTD.

Further, also silicon-based cross-coupling reagents in which silicon is connected to $sp^2$ carbon is greatly expected due to its selectivity of cross-coupling reaction, less toxicity, ease of preparation (see Non-Patent Document 1 (Armin de Meijere, François Diederich, Metal-Catalyzed Cross-Coupling Reactions, 2nd Edition, 2004 WILEY-VCH Verlag GmbH&Co.KGaA, Weinheim, p 163-216) or a similar document for example).

Of the silicon-based cross-coupling reagents, those in which all groups bound to silicon are organic groups are highly stable, but it is necessary to use an expensive fluoride ion as activators in using such silicon-based reagents to undergo the cross-coupling reaction. A method which requires no fluoride ions has been reported (see Non-Patent Document 2 (J. Org. Lett. 2002, 4, 3635-3638) and Non-Patent Document 3 (J. Org. Chem. 2004, 69, 8971-8974) or a similar document for example), but it is necessary to use a stoichiometric amount of transition metal promoters or strong bases.

Then, it has been reported that the cross-coupling reaction can be carried out without any fluoride ions by using: a silicon-based cross-coupling reagent in which organic groups on a silicon atom are partially substituted by halogens such as chlorine and fluorine atoms (see Patent Document 1 (Japanese Unexamined Patent Application No. 310972/1996 (Tokukaihei 8-310972) (Publication date: Nov. 26, 1996)) and Patent Document 2 (Japanese Unexamined Patent Application No. 283521/1992 (Tokukaihei 4-283521) (Publication date: Oct. 8, 1992)), Non-Patent Document 4 (Tetrahedron Lett. 1997, 38, 439-442), or a similar document for example); a silicon-based cross-coupling reagent in which organic groups on a silicon atom are partially substituted by alkoxyl groups (see Patent Document 2, Non-Patent Document 5 (Org. Lett. 2004, 6, 1147-1150), or a similar document for example); a silanol serving as a silicon-based cross-coupling reagent (see Non-Patent Document 6 (J. Org. Chem. 2000, 65, 5342-5349) or a similar document for example); and the like.

On the other hand, a cross-coupling reaction using intramolecular activation has also been reported (see Non-Patent Document 7 (J. Org. Chem. 2002, 67, 8450-8456), Non-Patent Document 8 (SYNLETT 2005, N0.1, pp 0176-0178), Non-Patent Document 9 (Chem. Pharm. Bull., 36(11) 4622-4625 (1988)), and Non-Patent Document 10 (Organic Letters, 2004, Vol. 6, No. 23, 4379-4381) or a similar document for example). Non-Patent Document 7 discloses a method in which an intramolecularly-activated intermediate obtained by reacting (Z)-γ-trimethylsilylallyl alcohol with copper (I)t-butoxide cross-couples with an aryl halide in the presence of a palladium catalyst. Non-Patent Document 8 reports that a cross-coupling reaction of trialkylvinylsilane activated intramolecularly by a (Z)-β-carboxyl group is carried out in the presence of a palladium catalyst without any fluoride ions. Non-Patent Document 9 reports that triethylammonium bis(catecolate)alkenylsiliconates in which pentacoordinate silicon atoms react with allyl iodide to generate cross-coupling products. Non-Patent Document 10 reports that a cross-coupling reaction of pentacoordinate allyl bis(catechol)silicates and aryl bromide can be carried out by microwave irradiation.

Further, it is reported that, although not on the cross-coupling reaction, pentacoordinate silicates generated by an intramolecular reaction of o-silylbenzyl alcohol decompose under mild conditions and a silyl or benzyl group is transferred to undergo an addition reaction to carbonyl compounds (see Non-Patent Document 11 (Can. J. Chem. 78:1421-1427 (2000)) or a similar document for example).

The silicon-based cross-coupling reagent has excellent selectivity in the cross-coupling reaction as described above, and is complementary to the boron-based one since the silicon-based protocol is often applicable to a target compound which is not accessible by the boron-based one. However, the silicon-based cross-coupling reagent which has a highly stabile tetraorganosilicon structure and undergoes a cross-coupling reaction under mild conditions without fluoride activation has not been produced.

Non-Patent Documents 2 and 3 discloses a protocol allowing use of such the highly stable silicon-based cross-coupling reagent having all organic groups and the cross-coupling reaction without any fluoride ions. However, it is necessary to use a stoichiometric amount of transition metal promoters or strong bases. Further, each of Patent Documents 1 and 2 and Non-Patent Documents 4, 5, and 6 discloses that organosilicon compounds having electron-withdrawing hetero atoms such as halogen and oxygen atoms on a silicon atom participate in the cross-coupling reaction without using any fluoride ions. Nevertheless, they are not stable toward moisture, acid or alkali, and thus, not easy to handle.

In the protocols described in Non-Patent Documents 7 and 8 utilizing intramolecular activation, it is necessary that a hydroxyl group or a carboxyl group is introduced in an organic group which is transferred in the cross-coupling reaction. Therefore, the transferable organic group on the silicon atom is limited to such structures. Silicon-based cross-coupling reagent containing a pentacoordinate silicon atom, which is disclosed in Non-Patent Document 9, requires longer reaction time to complete the cross-coupling reaction, resulting in an insufficient yield. According to Non-Patent Document 10, it is necessary to irradiate a microwave, so that a device for irradiating the microwave is required and some troubles are caused in operating the device.

Non-Patent Document 11 describes that intramolecular activation is used merely to carry out an addition reaction to the carbonyl compound.

On the other hand, in the boron-based cross-coupling reagent used frequently for the cross-coupling reaction, a boron residue is difficult to recover and reuse, whereas there has been a strong need to develop a cross-coupling protocol which allows reuse of reagents in view of effective utilization of resources, reduction of environmental loading, and the like.

The present invention was made in view of the foregoing problems, and the object of the present invention is to provide (i) silicon-based cross-coupling reagents which have high stability and allow for the cross-coupling reaction under mild conditions without using any fluoride ions and (ii) a synthetic method of organic compounds using the organosilicon reagents.

DISCLOSURE OF INVENTION

In order to solve the foregoing problems, a silicon-based cross-coupling reagent according to the present invention is an organosilicon compound reacting with an organic compound having a halogen or a pseudo halogen in the presence of a palladium catalyst and a base to form a carbon-carbon bond between a carbon atom connected to the leaving group and a carbon atom bound to a silicon atom of the organosilicon compound in accordance with a cross-coupling reaction, said silicon-based cross-coupling reagent being characterized in that: the silicon-based cross-coupling reagent has a structure represented by any one of the following formulas (1), (14), (15), (16), (17), (18), and (19),

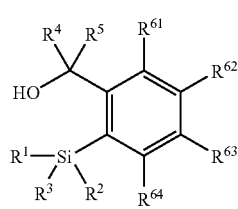

(1)

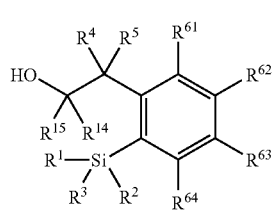

(14)

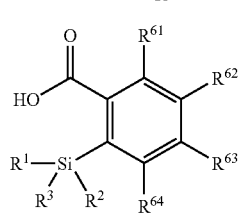

(15)

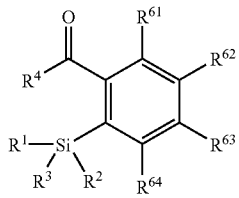

(16)

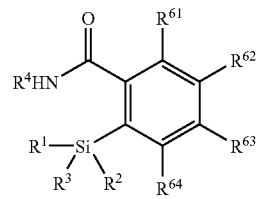

(17)

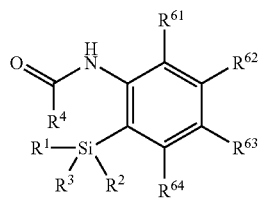

(18)

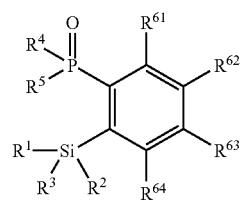

(19)

where $R^1$ represents a linear, branched, or cyclic hydrocarbon group having a substituent or no substituent or a heterocyclic group having a substituent or no substituent, and each of $R^2$ and $R^3$ represents an alkyl group in an independent manner, and each of $R^4$, $R^5$, $R^{14}$, $R^{15}$, $R^{61}$, $R^{62}$, $R^{63}$, and $R^{64}$ represents a hydrogen atom or a substituent in an independent manner.

It is preferable to arrange the silicon-based cross-coupling reagent according to the present invention so that $R^1$ has at least one double bond, and an $R^1$ atom connected to a silicon atom is $sp^2$ carbon.

The silicon-based cross-coupling reagent according to the present invention may be arranged so that the silicon-based cross-coupling reagent has a structure represented by the following formula (2)

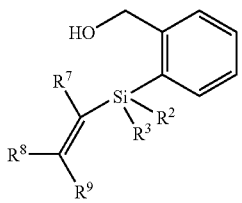

(2)

where each of $R^2$ and $R^3$ represents in an independent manner a linear or branched alkyl group whose carbon number is 1 to 6, and each of $R^7$, $R^8$, and $R^9$ represents in an independent manner a hydrogen atom, a linear or branched alkyl group which has or does not have a substituent and whose carbon number is 1 to 10, or an aryl group whose carbon number is 6 to 10.

Further, the silicon-based cross-coupling reagent according to the present invention may be arranged so that $R^1$ represents an aryl group which has or does not have a substituent and whose carbon number is 6 to 10 or a heterocyclic group which has or does not have a substituent.

Further, a compound according to the present invention is characterized by having a structure represented by any one of the following chemical formulas 1a, 1b, 1c, 1d, 1e, 1f, 1g, 1h, 1i, 2a, 2b, 2c, 2d, and 2e.

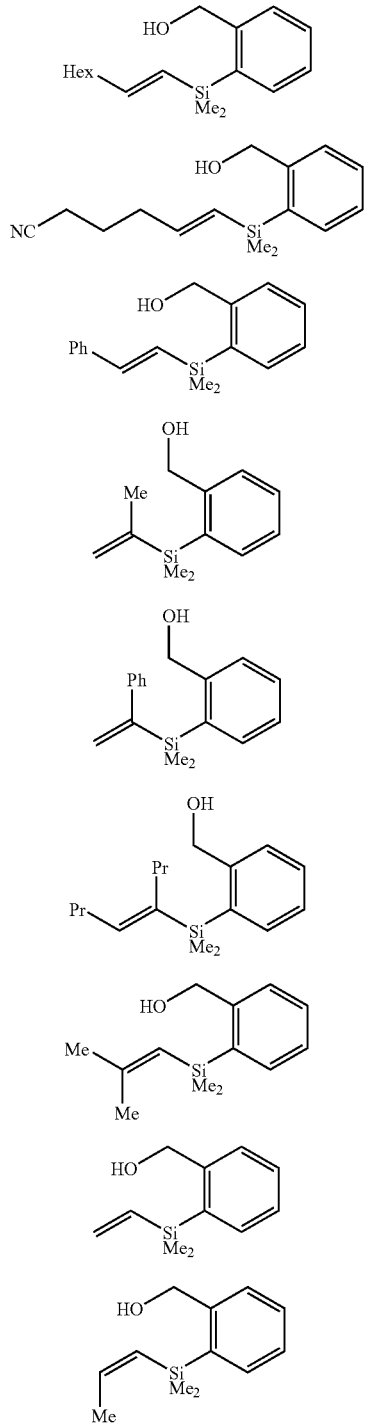

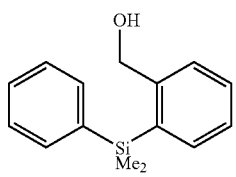

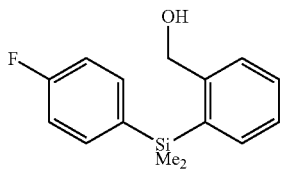

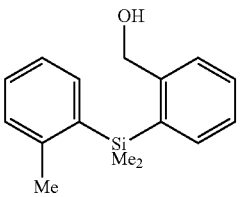

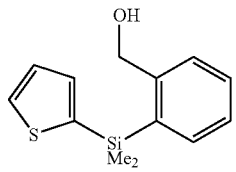

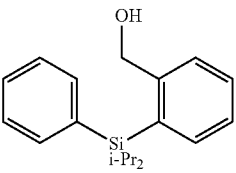

Further, a method according to the present invention for producing an organic compound is characterized by comprising a cross-coupling step in which a cross-coupling reaction between the silicon-based cross-coupling reagent as set forth in any one of claims 1 to 4 and an organic compound having a halogen or a pseudo halogen group is carried out in the presence of a palladium catalyst and a base.

Further, the method according to the present invention for producing the organic compound may further comprise a isolation step in which the residue of the silicon-based cross-coupling reagent is recovered.

A compound according to the present invention may have a structure represented by any one of the following chemical formulas p8, p9, p14, p19, p21, and p22.

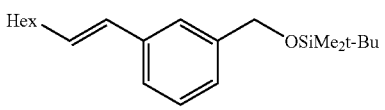

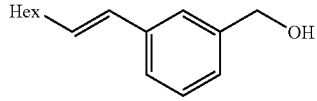

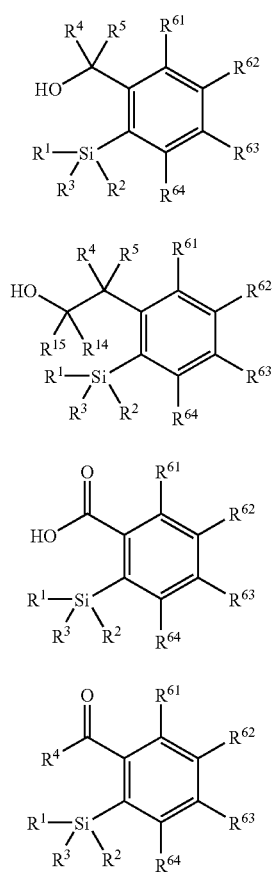

EFFECTS OF THE INVENTION

As described above, the silicon-based cross-coupling reagent according to the present invention has a structure represented by any one of the following formulas (1), (14), (15), (16), (17), (18), and (19),

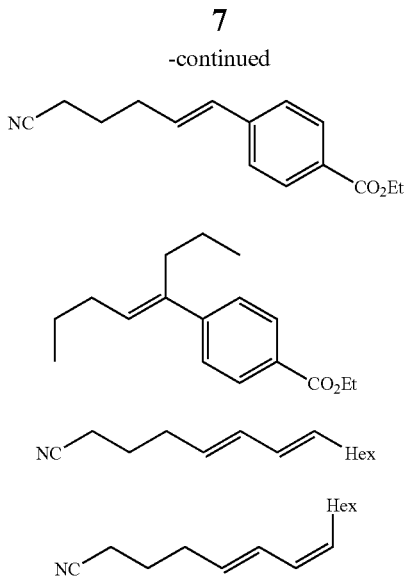

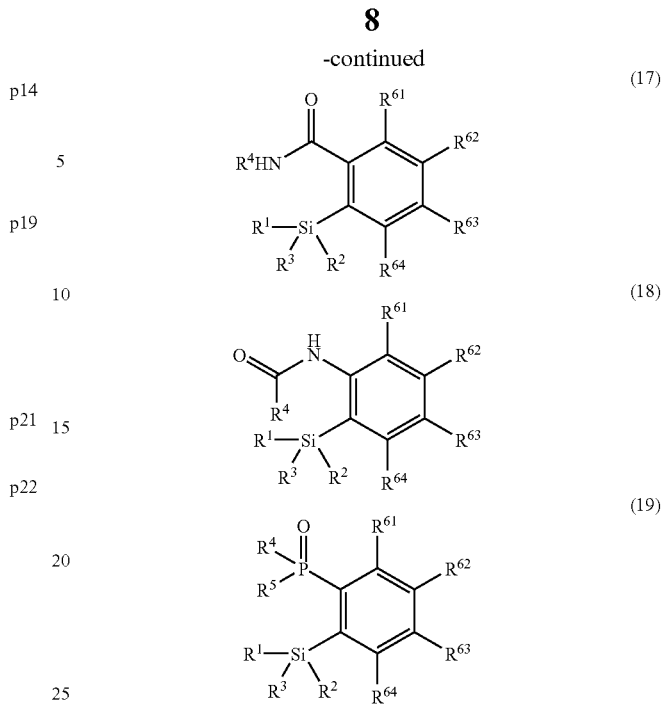

where $R^1$ represents a linear, branched, or cyclic hydrocarbon group having a substituent or no substituent or a heterocyclic group having a substituent or no substituent, and each of $R^2$ and $R^3$ represents an alkyl group in an independent manner, and each of $R^4$, $R^5$, $R^{14}$, $R^{15}$, $R^{61}$, $R^{62}$, $R^{63}$, and $R^{64}$ represents a hydrogen atom or a substituent in an independent manner, and all groups connected to a silicon atom are organic groups, so that high stability is realized. Further, as in the o-hydroxymethylphenyl group of the formula (1), a group containing an oxygen atom which allows for formation of an intramolecularly-activated pentacoordinate structure of the silicon atom, is included, so that it is possible to carry out the cross-coupling reaction under mild conditions. Further, it is possible to collect and reuse the residue of the silicon-based cross-coupling reagent, thereby realizing effective utilization of resources, reduction of environmental loading.

BEST MODE FOR CARRYING OUT THE INVENTION

The following describes an embodiment of the present invention. In view of the foregoing problems, the inventors of the present invention diligently studied to first find it possible to carry out the cross-coupling reaction under mild conditions with silicon-based cross-coupling reagents, in which all groups attached to a silicon atom are organic groups or hydrogen atoms. This can be realized by using silicon-based cross-coupling reagents in which a phenyl group is connected to a silicon atom and has a group containing an oxygen atom working in an intramolecular activation so that the group is ortho-positioned relative to the silicon atom. The following descriptions will explain (i) Silicon-based cross-coupling reagent according to the present invention and (II) Synthetic method of an organic compound using the silicon-based cross-coupling reagents of the present invention in this order.

(I) Silicon-Based Cross-Coupling Reagents According to the Present Invention (I-1) Silicon-Based Cross-Coupling Reagents The silicon-based cross-coupling reagents according to the present invention have a structure represented by any one of the following general formulas (14), (15), (16), (17), (18), and (19).

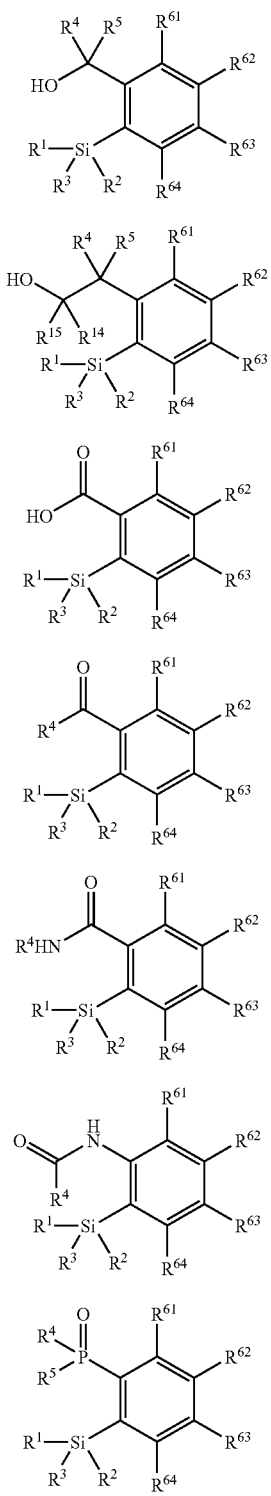

In the general formulas (14), (15), (16), (17), (18), and (19), $R^1$ represents a linear, branched, or cyclic hydrocarbon group having a substituent or no substituent or a heterocyclic group having a substituent or no substituent, and each of $R^2$ and $R^3$ represents an alkyl group in an independent manner, and each of $R^4$, $R^5$, $R^{14}$, $R^{15}$, $R^{61}$, $R^{62}$, $R^{63}$, and $R^{64}$ represents a hydrogen atom or a substituent in an independent manner.

In this manner, the silicon-based cross-coupling reagent of the present invention is such that all groups connected to a silicon atom are organic groups, so that its stability is high. Further, the silicon-based cross-coupling reagent includes a phenyl group connected to a silicon atom and having a group containing an oxygen atom working in an intramolecular activation and ortho-positioned relative to the silicon atom, enabling the cross-coupling reaction under mild conditions. Details of the mechanism have not been clarified, but the following assumption is given by taking general formula (1) as an example of the silicon-based cross-coupling reagents. That is, the cause may be such that a hydroxyl group of an o-hydroxymethylphenyl group connected to the silicon atom facilitates the formation of a pentacoordinate structure, which results in formation of an intramolecularly-activated intermediate.

The silicon-based cross-coupling reagent of the present invention reacts with an organic compound having a halogen or a pseudo halogen group in the presence of a palladium catalyst and a base to form a carbon-carbon bond between a carbon atom connected to the leaving group and a carbon atom bound to the silicon atom of the organosilicon compound. That is, the silicon-based cross-coupling reagent of the present invention and an organic compound $X\!-\!R^{10}$ having a halogen or a pseudo halogen group X are reacted with each other in accordance with a cross-coupling reaction, thereby producing an organic compounds $R^1\text{-}R^{10}$, i.e., cross-coupling products. Thus, it is possible to produce desired organic compounds $R^1\text{-}R^{10}$ by suitably selecting $R^1$ and $R^{10}$. Note that, $R^{10}$ is not particularly limited as long as $R^{10}$ is an organic group, i.e., any organic group may be used as $R^{10}$. Further, a carbon atom connected to the halogen or the pseudo halogen group X may be an $sp^2$, sp, or $sp^3$ carbon. Thus, in case where the $R^1$ carbon atom connected to the silicon atom is the $sp^2$ carbon, it is possible to form an $sp^2$-sp, $sp^2$-$sp^2$, or $sp^2$-$sp^3$ carbon bond. In case where the $R^1$ carbon atom connected to the silicon atom is the sp carbon, it is possible to form sp-sp, sp-$sp^2$, and sp-$sp^3$ carbon bonds. In case where the $R^1$ carbon atom connected to the silicon atom is the $sp^3$ carbon, it is possible to form an $sp^3$-sp, $sp^3$-$sp^2$, or $sp^3$-$sp^3$ carbon bond. Further, preferable examples of the halogen include a chlorine, bromine, and/or iodine atom. Further, examples of the pseudo halogen group include an alkylsulfonyloxy group, an arylsulfonyloxy group, and the like.

The silicon-based cross-coupling reagent of the present invention may be arranged in any manner as long as (i) the phenyl group connected to a silicon atom and having a group containing an oxygen atom usable in intramolecular activation so that the group is ortho-positioned relative to the silicon atom (e.g., o-hydroxymethylphenyl group), (ii) $R^2$ and $R^3$ representing an alkyl group in an independent manner, and (iii) $R^1$ representing an organic group whose cross-coupling reaction is to be carried out are connected to a silicon atom.

The aforementioned $R^2$ and $R^3$ are not particularly limited as long as each of them represents an alkyl group in an independent manner, but it is more preferable that each of $R^2$ and $R^3$ represents a linear or branched alkyl group whose carbon number is 1 to 6. Specific examples of the alkyl group include a methyl group, an ethyl group, a propyl group, an isopropyl group, a butyl group, an isobutyl group, a sec-butyl group, a tert-butyl group, a pentyl group, a hexyl group, and the like.

Further, in the silicon-based cross-coupling reagent of the present invention, each of the aforementioned $R^4$, $R^5$, $R^{14}$, $R^{15}$, $R^{61}$, $R^{62}$, $R^{63}$, and $R^{64}$ represents a hydrogen atom or a substituent in an independent manner. That is, the silicon-based cross-coupling reagent of the present invention may be arranged in any manner as long as a phenyl group connected to a silicon atom and having a group containing an oxygen atom usable in intramolecular activation so that the group is ortho-positioned relative to the silicon atom thereby allowing intramolecular activation. Thus, the phenyl group having the group containing the oxygen atom usable in intramolecular activation so that the group is ortho-positioned relative to the silicon atom may have a substituent or may have no substituent. Further, any substituent may be contained as long as the substituent does not have unfavorable influence on the intramolecular activation or the cross-coupling reaction. Further, the number of substituents of the phenylene group in the aforementioned o-hydroxyphenyl methylphenyl group is not particularly limited. Such a substituent is not particularly limited, but examples thereof include: hydrocarbon group such as aryl group, alkenyl group, alkyl group, alkynyl group, alkadienyl group, alkatrienyl group, alkadiynyl group, and alkatriynyl group; heterocyclic group; cyano group; formyl group, alkoxycarbonyl group, and carboxyl group; phosphate group; sulfo group; hydroxy group; sulfonyl group; halogen; acyl group such as alkanoyl group, alkenoyl group, and alkynoyl group; alkoxy group, amino group, nitro group, imino group, trialkylsiloxy group, hydroxyalkyl group, and the like.

The aforementioned $R^1$ is an organic group usable in the cross-coupling reaction, and a desired organic group can be selected from various organic groups. The $R^1$ is not particularly limited as long as $R^1$ is a hydrocarbon group having a substituent or no substituent. Further, a carbon atom of the hydrocarbon group may be partially substituted by O, N, P, S, Si, or the like. Above all, it is more preferable that $R^1$ is a linear, branched, or cyclic hydrocarbon group having a substituent or no substituent or a heterocyclic group having a substituent or no substituent.

The linear, branched, or cyclic hydrocarbon group may be saturated or unsaturated, the number and position(s) of double bond(s) or triple bond(s) included are not particularly limited. Further, the number of carbon atom(s) is not particularly limited, but the number is more preferably 1 to 100, still more preferably 1 to 10. Examples of such a hydrocarbon group include aryl group, alkenyl group, alkyl group, alkinyl group, alkadienyl group, alkatrienyl group, alkadiynyl group, alkatriynyl group, and the like.

The aryl group may be a monocyclic aryl group, a polycyclic aryl group, or a ring-condensed aryl group, as long as the aryl group is an aromatic hydrocarbon group. Such an aryl group is not particularly limited, but the aryl group more preferably contains 6 to 50 carbon atoms in its molecule, still more preferably contains 6 to 10 carbon atoms in its molecule. Specific examples of such an aryl group include phenyl group, tolyl group, xylyl group, cumenyl group, mesityl group, 1-naphtyl group, 2-naphtyl group, antholyl group, phenantholyl group, and the like.

Further, the alkenyl group may be a linear alkenyl group, a branched alkenyl group, or a cyclic alkenyl group, and is not particularly limited. Such an alkenyl group is more preferably an alkenyl group containing 2 to 100 carbon atoms in its molecule, still more preferably an alkenyl group containing 2 to 10 carbon atoms in its molecule. Specific examples of such an alkenyl group include vinyl group, allyl group, 1-propenyl group, 2-propenyl group, isopropenyl group, butenyl group, isobutenyl group, pentenyl group, isopentenyl group, hexenyl group, isohexenyl group, heptenyl group, isoheptenyl group, octenyl group, isooctenyl group, nonenyl group, isononenyl group, decenyl group, isodecenyl group, cyclopentenyl group, cyclohexenyl group, cyclopeptenyl group, cyclooctenyl group, and the like.

Further, the alkyl group may be a linear alkyl group, a branched alkyl group, or a cyclic alkyl group, and is not particularly limited. Such an alkyl group is not particularly limited, but the alkyl group is more preferably an alkyl group containing 1 to 100 carbon atoms in its molecule, more preferably an alkyl group containing 1 to 10 carbon atoms in its molecule. Specific examples of such an alkyl group include methyl group, ethyl group, propyl group, isopropyl group, butyl group, isobutyl group, sec-butyl group, tert-butyl group, pentyl group, hexyl group, heptyl group, octyl group, nonyl group, decyl group, cyclopropyl group, cyclobutyl group, cyclopentyl group, cyclohexyl group, cycloheptyl group, cyclooctyl group, and the like.

The alkynyl group may be a linear alkynyl group, a branched alkynyl group, or a cyclic alkynyl group, and is not particularly limited. Such an alkylnyl group is not particularly limited, but the alkynyl group is more preferably an alkynyl group containing 2 to 100 carbon atoms in its molecule, and still more preferably an alkynyl group containing 2 to 10 carbon atoms in its molecule. Specific examples of such an alkynyl group include ethynyl group, 1-propynyl group, 2-propynyl group, butynyl group, petynyl group, hexynyl group, heptynyl group, octynyl group, cyclohexylethynyl group, cycloheptylethynyl group, cyclooctylethynyl group, arylethynyl group, and the like.

Further, the alkadienyl group may be a linear alkadienyl group, a branched alkadienyl group, or a cyclic alkadienyl group, and is not particularly limited. Such an alkadienyl group is more preferably an alkadienyl group containing 4 to 100 carbon atoms in its molecule, still more preferably an alkadienyl group containing 4 to 10 carbon atoms in its molecule. Specific examples of such an alkadienyl group include butanedienyl group, pentadienyl group, hexadienyl group, heptadienyl group, octadienyl group, nonadienyl group, decanedienyl group, cyclopentandienyl group, cyclohexadienyl group, cyclopeptadienyl group, cyclooctadienyl group, and the like.

Further, the alkadiynyl group may be a linear alkadiynyl group, a branched alkadiynyl group, or a cyclic alkadiynyl group, and is not particularly limited. Such an alkadiynyl group is more preferably an alkadiynyl group containing 4 to 100 carbon atoms in its molecule, still more preferably an alkadiynyl group containing 4 to 10 carbon atoms in its molecule. Specific examples of the alkadiynyl group include butanediynyl group, pentadiynyl group, hexadiynyl group, heptadiynyl group, octadiynyl group, nonadiynyl group, decanediynyl group, aryldiynyl group, and the like.

The heterocyclic group may be saturated or unsaturated, and may be a monocyclic group, a polycyclic group, or a ring-condensed group. A kind and the number of hetero atoms are not particularly limited, and examples thereof include sulfur atom, nitrogen atom, oxygen atom, silicon atom, phosphate atom, and the like. For example, a 5-6 membered monocyclic heterocyclic group is contained. Specific examples of such a heterocyclic group include furyl group, pyridyl group, quinolyl group, thienyl group, piperidyl group, isoquinolyl group, pyrolyl group, pyrazolyl group, isooxazolyl group, isothiazolyl group, imidazolyl group, oxazolyl group, thiazolyl group, pyridazyl group, pyrimydyl group, pyradyl group, indolyl group, and the like.

Further, the hydrocarbon group or the heterocyclic group may be not-substituted or may be substituted. Such a substituent is not particularly limited, but examples thereof include: hydrocarbon group such as aryl group, alkenyl group, alkyl group, alkynyl group, alkadienyl group, alkatrienyl group, alkadiynyl group, and alkatriynyl group; heterocyclic group; cyano group; formyl group, alkoxycarbonyl group, and carboxyl group; phosphate group; sulfo group; hydroxy group; sulfonyl group; halogen; acyl group such as alkanoyl group, alkenoyl group, and alkynoyl group; alkoxy group, amino group, nitro group, imino group, trialkylsiloxy group, hydroxy alkyl group, and the like.

Further, it is more preferable that $R^1$ has at least one double bond and an $R^1$ atom connected to a silicon atom is an $sp^2$ carbon. This allows for formation of an $sp^2$-$sp^2$ carbon bond. Hence, the cross-coupling reaction allows for construction of a π-conjugated system serving as a key compound of a medical intermediate and a molecular-scale electronics element.

An example of such a silicon-based cross-coupling reagent that $R^1$ has at least one double bond and the $R^1$ atom connected to the silicon atom is an $sp^2$ carbon is the aforementioned aryl group having a substituent or no substituent. In such an aryl group, position(s) or the number of substituent(s) are not particularly limited.

Another example of such a silicon-based cross-coupling reagent that $R^1$ has at least one double bond and the $R^1$ atom connected to the silicon atom is an $sp^2$ carbon is represented by the following general formula (2).

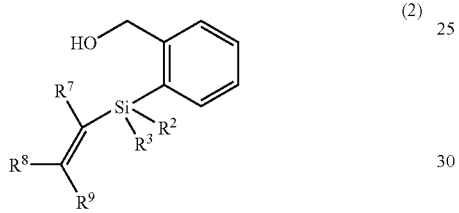

(2)

In the general formula (2), each of $R^2$ and $R^3$ represents in an independent manner a linear or branched alkyl group whose carbon number is 1 to 6. The linear or branched alkyl group whose carbon number is 1 to 6 is the same as in the general formula (1). Further, in the general formula (2), each of $R^7$, $R^8$, and $R^9$ represents in an independent manner a hydrogen atom, an aryl group having a substituent or no substituent, an alkenyl group having a substituent or no substituent, an alkinyl group having a substituent or no substituent, an alkyl group having a substituent or no substituent, or a heterocyclic group having a substituent or no substituent, and are not particularly limited. However, it is more preferable that each of $R^7$, $R^8$, and $R^9$ represents in an independent manner a hydrogen atom, a linear or branched alkyl group which has or does not have a substituent and whose carbon number is 1 to 10, or an aryl group which has or does not have a substituent and whose carbon number is 6 to 10. The aryl group, the alkenyl group, the alkinyl group, the alkyl group, the heterocyclic group, the linear or branched alkyl group whose carbon number is 1 to 10, and the aryl group whose carbon number is 6 to 10 are the same as in the general formula (1). Further, examples of the substituent include: hydrocarbon group such as aryl group, alkenyl group, alkyl group, alkinyl group, alkadienyl group, alkatrienyl group, alkadiynyl group, and alkatriynyl group; heterocyclic group; cyano group; formyl group, alkoxycarbonyl group, and carboxyl group; phosphate group; sulfur group; hydroxy group; sulfonyl group; halogen; acyl group such as alkanoyl group, alkenoyl group, and alkynoyl group; alkoxy group, amino group, nitro group, imino group, trialkylsiloxy group, hydroxy alkyl group, and the like.

Further, the silicon-based cross-coupling reagent according to the present invention refers to a substance serving not only as a novel cross-coupling reagent but also as a novel compound. Thus, also such a novel compound is included in the present invention. An example of the compound according to the present invention is a compound having a structure represented by any one of the following general formula 1a, 1b, 1c, 1d, 1e, 1f, 1g, 1h, 1i, 2a, 2b, 2c, 2d, and 2e.

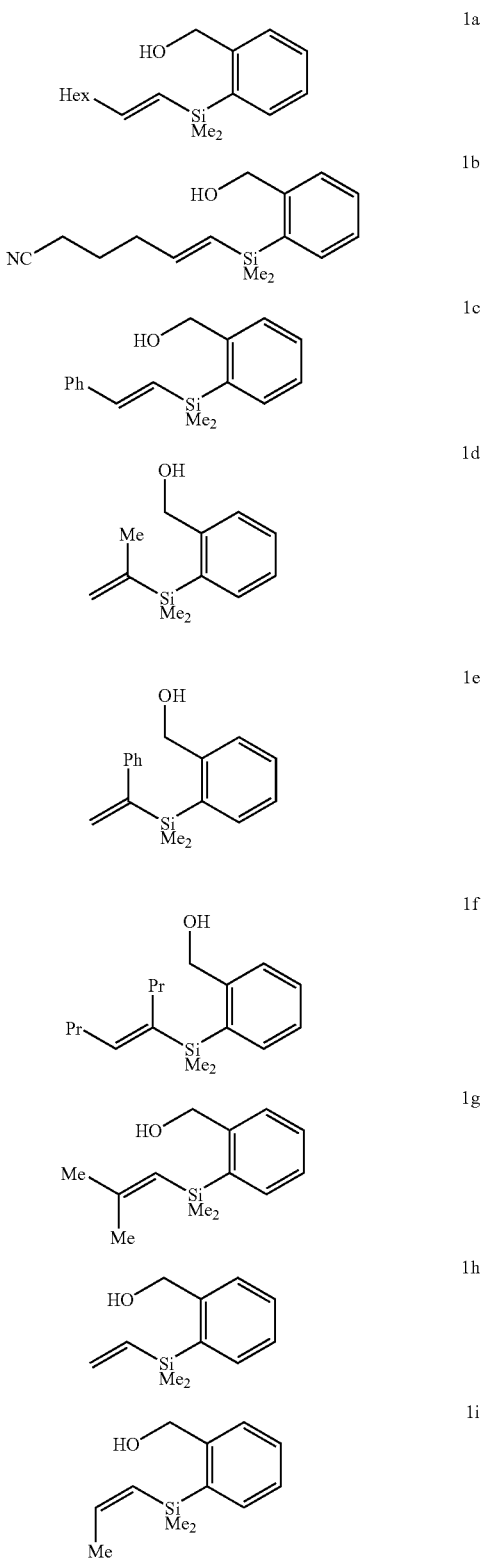

-continued

2a
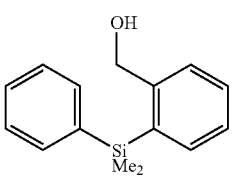

2b
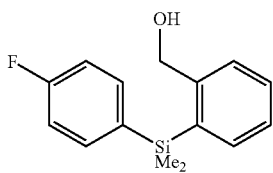

2c
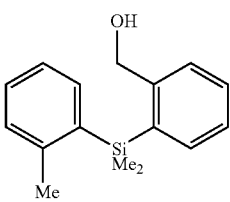

2d
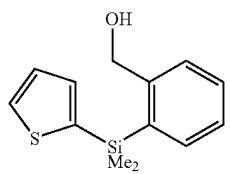

2e
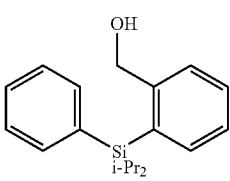

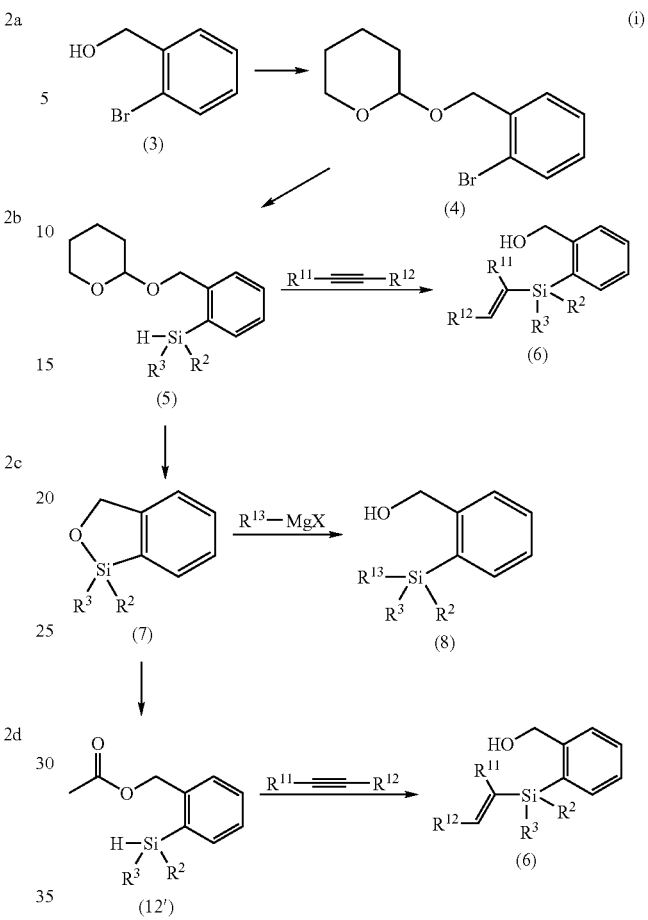

Such a compound can be used as the cross-coupling reagent. Further, the compound is extremely useful particularly as a cross-coupling reagent which has high stability and allows a cross-coupling reaction under mild conditions giving a silicon residue which can be collected and reused.

(I-2) Production Method of the Silicon-Based Cross-Coupling Reagent

The method according to the present invention for producing the silicon-based cross-coupling reagent is not particularly limited, and it is possible to produce the silicon-based cross-coupling reagent by suitably adopting a conventionally known method.

The method according to the present invention for producing the silicon-based cross-coupling reagent is not particularly limited. However, in producing the silicon-based cross-coupling reagent represented by the general formula (1), it is possible to adopt a method indicated by the following reaction formula (i) with a 2-bromophenylmethanol (3) used as a starting material.

As expressed by the reaction formula (i), first, 2-bromophenylmethanol (3) is reacted with 3,4-dihydro-2H-pyran, for example, in the presence of acid such as hydrochloric acid, thereby obtaining 2-(2-tetrahydro-2H-pyranoxymethyl)bromobenzene (4). The resultant 2-(2-tetrahydro-2H-pyranoxymethyl)bromobenzene (4) is reacted with, for example, chlorodialkylsilane in the presence of organic lithium, thereby obtaining dialkyl[2-(2-tetrahydro-2H-pyranoxymethyl)phenyl]silane (5).

The resultant dialkyl[2-(2-tetrahydro-2H-pyranoxymethyl)phenyl]silane (5) is reacted with an organic group having at least one triple bond in the presence of a platinum catalyst as expressed by the reaction formula (i) for example. In this way, it is possible to produce the silicon-based cross-coupling reagent of the present invention. In case where two carbon atoms having the triple bond therebetween are respectively connected to $R^{11}$ and $R^{12}$ for example, it is possible to produce the silicon-based cross-coupling reagent represented by the general formula (6). Note that, by suitably selecting the organic group with which the reaction is to be carried out, it is possible to produce the silicon-based cross-coupling reagent having a desired organic group with which the cross-coupling reaction is to be carried out.

Further, a silicon-based cross-coupling reagent may be produced by using oxasilacyclopentane (7) obtained by reacting the dialkyl[2-(2-tetrahydro-2H-pyranoxymethyl)phenyl]silane (5) with p-toluenesulfonic acid monohydrate for example. In such a method, for example, a Grignard reagent $R^{13}{}_m$-$M''X_{n-m}$ having a desired organic group $R^{13}$ with which the cross-coupling reaction is to be carried out is reacted with the oxasilacyclopentane (7), thereby obtaining the silicon-based cross-coupling reagent of the present invention. Note that, M is not particularly limited as long as it is a metal atom, but examples thereof include Mg, Al, As, Ge, Hg, Pb, Sn, Te, Zn, and the like. Above all, it is more preferable that M is Mg or Al. Further, it is preferable that X is a halogen atom such as Cl, Br, I, and the like.

Further, the silicon-based cross-coupling reagent may be produced by using dimethyl(2-(acetoxymethyl)phenyl)silane (12') obtained by reacting the oxasilacyclopentane (7) with an acetylation agent such as acetyl chloride after the reaction with a reducing agent such as lithium aluminum hydride for example. In such a method, the dimethyl(2-(acetoxymethyl)phenyl)silane (12') is reacted with an organic group having at least one triple bond in the presence of a platinum catalyst as expressed by the reaction formula (i) for example, thereby producing the silicon-based cross-coupling reagent of the present invention.

(II) Method of the Present Invention for Producing an Organic Compound Using the Silicon-Based Cross-Coupling Reagent A cross-coupling reaction of the silicon-based cross-coupling reagent according to the present invention is carried out with an organic compound having a halogen or a pseudo halogen group in the presence of a palladium catalyst and a base, thereby forming a carbon-carbon bond between a carbon atom connected to the leaving group and a carbon atom connected to the silicon atom of the silicon-based cross-coupling reagent. Thus, also the method for producing the organic compound having the carbon-carbon bond by using the silicon-based cross-coupling reagent of the present invention is included in the present invention.

The production method of the organic compound may be arranged in any manner as long as the method includes at least a cross-coupling step in which the silicon-based cross-coupling reagent of the present invention and the organic group having a halogen or a pseudo halogen group are reacted with each other in the presence of a palladium catalyst and a base in accordance with a cross-coupling reaction. Further, the method of the present invention for producing the organic compound may further include an isolation step (collection step) in which the silicon residue of the cross-coupling reagent is recovered. The following demonstrates (II-1) Cross-coupling step and (II-2) Isolation step in this order.

(II-1) Cross-Coupling Step

In the cross-coupling step, the silicon-based cross-coupling reagent of the present invention and an organic compound (9) having a halogen or a pseudo halogen group X are reacted with each other in the presence of a palladium catalyst and a base as expressed by the following reaction formula (ii).

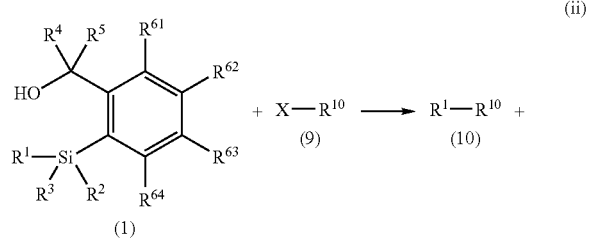

(ii)

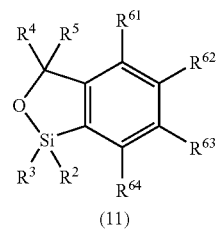

(11)

Note that, the reaction formula (ii) indicates a reaction in case where the silicon-based cross-coupling reagent of the present invention (1) is used, but this is applicable also to cases of silicon-based cross-coupling reagents (14), (15), (16), (17), (18), and (19).

As a result, a carbon-carbon bond between a carbon atom connected to the leaving group and a carbon atom connected to the silicon atom of the silicon-based cross-coupling reagent is formed, thereby producing organic compounds $R^1$-$R^{10}$. Further, by using the silicon-based cross-coupling reagent of the present invention, it is possible to realize high stability of the silicon-based cross-coupling reagent used and carry out the cross-coupling reaction under mild conditions.

In the organic compound (9) which is used in the present invention and has a halogen or pseudo halogen group X (hereinafter, referred to as "organic electrophile" in the present specification), preferable examples of the leaving group X include halogen such as chlorine, bromine, and iodine atom; alkylsulfonyloxy group ($-O-S(O)_2-R^{14}$) (where $R^{14}$ represents an alkyl group); an arylsulfonyloxy group ($-O-S(O)_2-R^{14}$) (where $R^{14}$ represents an aryl group); and the like.

Further, $R^{10}$ of the organic electrophile (9) is not particularly limited and may be an any organic group as long as it is an organic group. Further, the carbon atom connected to the leaving group X may be an $sp^2$, sp, or $sp^3$ carbon.

The $R^{10}$ is not particularly limited and may be an alkyl group having a substituent or no substituent. Further, the $R_1$ may be an alkyl group wherein carbon atoms of the group may be partially substituted by O, N, P, S, Si, and the like. Above all, it is more preferable that $R^1$ is a linear, branched, or cyclic hydrocarbon group having a substituent or no substituent or a heterocyclic group having a substituent or no substituent. The linear, branched, or cyclic hydrocarbon group having a substituent or no substituent or the heterocyclic group having a substituent or no substituent is the same as in the hydrocarbon group and the heterocyclic group that were described in the foregoing item (I-1), so that descriptions thereof are omitted.

Further, also an amount of the organic electrophile (9) used is not particularly limited. However, with respect to 1 mol of the silicon-based cross-coupling reagent, the amount of the organic electrophile (9) is 0.05 mol or more and 20 mol or less, more preferably 0.5 mol or more and 3 mol or less. By setting the amount of the organic electrophile (9) within the foregoing range, it is possible to prevent the silicon-based cross-coupling reagent and the organic electrophile from being wasted.

Further, the present step is carried out in the presence of the palladium catalyst and the base. Examples of the palladium catalyst include $PdCl_2$, $PdCl_2(CH_3CN)_2$, $Pd_2(dpa)_3$, (Pd(PPh_3)_4$, $Pd(Ph_2PCH_3)_4$, $PdCl_2(PPh_3)_2$, $(PdCl_2[P(o-tolyl)_3]_2$, $PdCl_2(P(cyclohexyl)_3)_2$, $PdCl_2(PEt_3)_2$, and the like. Further, a catalyst actually associated with the cross-coupling reaction in a reaction system may be prepared by mixing $PdCl_2$, Pd(OAc)$_2$, Pd$_2$(dba)$_3$, and the like with a suitable ligand in the reaction system. Examples of the ligand include: P(o-tolyl)$_3$; P(i-Pr)$_3$; PPh$_3$; Ph$_2$PCH$_3$; P(2-furyl)$_3$; N-(2-diphenylphosphinobenzyliden)alkylamine such as N-(2-diphenylphosphinobenzyliden)cyclohexylamine; N-(2-diphenylphoshinobenzyliden)arylamine; P(cyclohexyl)$_3$; P(o-MeOPh)$_3$; P(p-MeOPh)$_3$; P(OEt)$_3$; P(O-p-tolyl)$_3$; P(O-o-tolyl)$_3$; P(O-i-Pr)$_3$; pyridine; 2,2'-bipyridyl; alkyl substituted pyridine; aryl substituted pyridine; triarylarsine; triarylantimony; and triarylbismuth.

Further, the palladium catalyst may be supported by a solid support. Examples of such a palladium catalyst include palladium carbon, palladium black, palladium cluster, and the like.

An amount of the catalyst used may vary depending on a kind of the silicon-based cross-coupling reagent with which the reaction is to be carried out and a kind of the organic electrophile (9). However, with respect to 1 mol of the silicon-based cross-coupling reagent, an amount of the palladium atoms is 0.001 mol or more and 0.2 mol or less, more preferably 0.005 mol or more and 0.05 mol or less, still more preferably 0.01 mol or more and 0.3 mol or less. If the amount of the catalyst is less than the foregoing range, a reaction rate of the cross-coupling reaction is low, which results in an insufficient yield. Further, if the amount of the catalyst is more than the foregoing range, catalytic effect is no more improved.

Further, the base used in the present step is not particularly limited as long as the base is a basic compound which can promote and facilitate the cross-coupling reaction. Such a base is not particularly limited, but examples thereof include potassium carbonate, sodium carbonate, cesium carbonate, barium hydroxide, potassium hydroxide, sodium hydroxide, potassium acetate, triethylamine, sodium methoxide, lithium methoxide, alkyllithium, sodium hydride, potassium hydride, and the like. An amount of the base used is not particularly limited. However, with respect to 1 mol of the silicon-based cross-coupling reagent, the amount of the base is 1 mol or more and 10 mol or less, more preferably 1 mol or more and 3 mol or less.

Further, in the present step, a univalent Cu compound may be added as necessary. Such a Cu compound is not particularly limited, but favorable examples thereof include CuI, CuBr, Cu(OH), CuCl, and the like. As a result, it is possible to enhance the yield and the reaction rate.

In the present step, a solvent used is not particularly limited, but it is preferable to use an organic solvent. In case of water used as the solvent, it may be difficult to dissolve a substrate and a catalyst, so that it is more preferable to use the organic solvent. Note that, water may be contained in the organic solvent. Specific examples of the organic solvent usable in the present step include: dimethylsulfoxide (DMSO); amide such as N,N-dimethylformamide (DMF), N,N-dimethylacetamide, N-methylpyrrolidone, and hexamethyl phosphoric acid triamide (HMPA); nitrites such as acetonitrile; alcohols such as methanol, ethanol, 1-propanol, 2-propanol, 1-butanol, 2-butanol, isobutylalcohol, and isopentylalcohol; ketones such as acetone, 2-butanone, 3-pentanone, methylisopropylketone, methyl propyl ketone, 3-hexanone, and methyl butyl ketone; ether such as diethylether, diisopropylether, tetrahydrofuran, and tetrahydropyran; lower saturated hydrocarbons such as pentane, hexane, and cyclohexane; esters such as ethyl acetate; and the like. Further, the solvent may be a mixture of one or more kinds of solvents. Above all, it is more preferable to use a polar solvent for the present step. By using the polar solvent, it is possible to favorably carry out the cross-coupling reaction. Examples of such a polar solvent include dimethylsulfoxide (DMSO); N,N-dimethylformamide (DMF); N,N-dimethylacetamide; N-methylpyrrolidone; hexamethyl phosphoric acid triamide (HMPA); ether such as tetrahydrofuran.

Further, an amount of the solvent used is not particularly limited. However, it is preferable to set the amount so that the concentration of the silicon-based cross-coupling reagent is 0.01 M or more and 10 M or less, more preferably 0.05 M or more and 5 M or less, still more preferably 0.1 M or more and 3 M or less. If the concentration of the solvent is less than 0.01 M, the reaction rate of the cross-coupling reaction is low. If the concentration of the solvent is more than 100 M, the reaction solution is uneven.

Also a reaction temperature of the cross-coupling reaction is not particularly limited, but the reaction temperature preferably ranges from 0 to 120° C., more preferably from 10 to 100° C. Further, a reaction time is not particularly limited, but it is preferable that the reaction time is one hour or more and 24 hours or less.

Further, in the cross-coupling reaction, an order in which the silicon-based cross-coupling reagent, the organic electrophile (9), the catalyst, the ligand, and the base are added is not particularly limited, and these materials may be added in any order. For example, it is possible to adopt a method in which the catalyst, the ligand, and the base are added to the solvent and the mixture is stirred and then the silicon-based cross-coupling reagent and the organic electrophile (9) are added thereto; a method in which the catalyst, the ligand, the base, the silicon-based cross-coupling reagent, and the organic electrophile (9) are simultaneously added to the solvent and the mixture is stirred; and a similar method. As to the method in which the catalyst, the ligand, and the base are added to the solvent and the mixture is stirred and then the silicon-based cross-coupling reagent and the organic electrophile (9) are added thereto, the silicon-based cross-coupling reagent may be added before addition of the organic electrophile (9) or the organic electrophile (9) may be added before addition of the silicon-based cross-coupling reagent, but it is preferable to sequentially add the silicon-based cross-coupling reagent and the organic electrophile (9).

In the present step, a carbon-carbon bond between the carbon atom connected to the leaving group of the organic electrophile (9) and the carbon atom connected to the silicon atom of the silicon-based cross-coupling reagent is formed, so that the organic compounds $R^1$-$R^{10}$ are generated. Thus, the silicon-based cross-coupling reagent and the organic electrophile (9) respectively having desired $R^1$ and $R^{10}$ are reacted with each other, thereby efficiently producing only desired organic compounds of various kinds.

Further, a novel organic compound can be produced in the present step. Thus, also the novel compound is included in the present invention. An example of the compound according to the present invention include a compound represented by any one of the following chemical formulas p8, p9, p14, p19, p21, and p22.

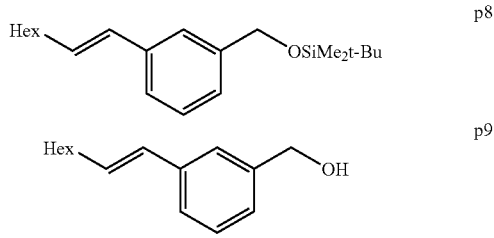

p14: NC~~~~~/=\\—C6H4—CO2Et p19: (structure with CO2Et)

p21: NC~~~~\=/\=/Hex p22: NC~~~~\=/\=/Hex (II-2) Isolation Step

The residue in silicon-based cross-coupling reagent of the present invention which is used in the method according to the present invention for producing the organic compound can be recovered and reused after the cross-coupling reaction. Thus, the method according to the present invention for producing the organic compound may further include the isolation step in which the silicon residue of the cross-coupling reagent is recovered.

The isolation step is not particularly limited as long as the silicon-based cross-coupling reagent is synthesized from oxasilacyclopentane (11) generated in the cross-coupling step as a by-product. An example thereof is a method represented by the following reaction formula (iii).

Further, the silicon-based cross-coupling reagent (13) of the present invention may be reproduced by reacting the oxasilacyclopentane (11) with a Grignard reagent $R^1{}_m$-$M''X_{n-m}$ having a desired organic group $R^1$ with which the cross-coupling reaction is to be carried out for example. Note that, M is not particularly limited as long as it is a metal atom. Examples thereof include Mg, Al, As, Ge, Hg, Pb, Sn, Te, Zn, and the like. Above all, it is more preferable that M is Mg or Al. Further, it is preferable that X is a halogen atom such as Cl, Br, I, and the like.

The present invention is not limited to the description of the embodiments above, but may be altered by a skilled person within the scope of the claims. An embodiment based on a proper combination of technical means disclosed in different embodiments is encompassed in the technical scope of the present invention.

EXAMPLES

The following Examples will more specifically explain the present invention, but the present invention is not limited to the Examples.

Note that, in the following Examples, flash column chromatography was carried out by using Merck silica gel 60 (230-400 mesh) or aluminum oxide 90 neutral (70-230 mesh). Further, analytical thin layer chromatography (TLC) was performed on Merck Kiesel gel 60 $F_{254}$ (0.25 mm) plate. Visualization was accomplished with UV light (254 nm) and/or an aqueous alkaline $KMnO_4$ solution followed by heating.

Further, proton and carbon nuclear magnetic resonance spectra ($^1H$ NMR and $^{13}C$ NMR) were recorded on a Varian Mercury 400 ($^1H$ NMR, 400 MHz; $^{13}C$ NMR, 101 MHz) or Varian Mercury 200 ($^1H$ NMR, 200 MHz; $^{13}C$, 50.3 MHz) spectrometer (both of which were products of Varian) with

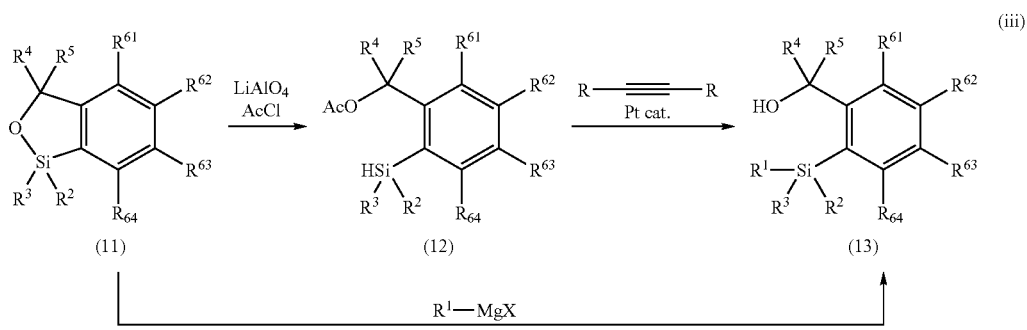

(iii)

Note that, the reaction formula (iii) indicates a case where the silicon-based cross-coupling reagent (1) of the present invention is used, but this is applicable also to cases of the silicon-based cross-coupling reagents (14), (15), (16), (17), (18), and (19). In such a method, for example, oxasilacyclopentane (11) is reacted with an acetylation agent such as acetyl chloride after the reaction with a reducing agent such as lithium aluminum hydride, thereby obtaining dimethyl(2-(acetoxymethyl)phenyl)silane (12). Note that, an acetomethoxymethylphenyl group of dimethyl(2-(acetoxymethyl)phenyl)silane (12) may contain substituents such as $R^4$, $R^5$, $R^{14}$, $R^{15}$, $R^{61}$, $R^{62}$, $R^{63}$, and $R^{64}$, as expressed by the reaction formula (iii). The dimethyl(2-(acetoxymethyl)phenyl)silane (12) is reacted with alkyne having various substituents or no substituent in the presence of a platinum catalyst for example, thereby reproducing the silicon-based cross-coupling reagent (13) of the present invention.

solvent resonance as the internal standard (1H HMR, $CHCl_3$ at 7.26 ppm or $C_6H_6$ at 7.15 ppm; $^{13}C$ NMR, $CDCl_3$ at 77.0 ppm or $C_6H_6$ at 128.0 ppm). A melting point thereof was measured by using YANAKO MP-500D (product of Yanagimoto Seisakusyo). A high resolution mass spectrum was measured by using JEOL JMS-700 (product of Nippon Denshi, EI and CI) or JEOL JMS-HX110A (product of Nippon Denshi, $FAB^+$).

Further, unless particularly mentioned, a commercial reagent was used without being purified. Diethylether, THF, and hexane were distilled from sodium/benzophenone ketyl. DMSO (product of Aldrich) was used without being further purified. N-(2-diphenylphosphino benzylidene)cyclohexylamine was prepared by a method described in Yoshida, H., Shirakawa, E., Kurahashi, T., Nakao, Y., Hiyama, T., Organometallics 2000, 19, 5671-5678.

Example 1

Preparation of Compounds for Producing Silicon-Based Cross-Coupling Reagent

In the present Example, 2-bromophenylmethanol was used as a starting substance to produce, in accordance with the method indicated by the reaction expression (i), dimethyl[2-(2-tetrahydro-2H-pyranoxymethyl)phenyl]silane (5), oxasilacyclopentane (7), dimethyl(2-(acetoxymethyl)phenyl)silane (12'), i.e., compounds for producing the silicon-based cross-coupling reagent.

Preparation of dimethyl[2-(2-tetrahydro-2H-pyranoxymethyl)phenyl]silane (5) ($R^2$ and $R^3$: methyl group)

Ten drops of concentrated hydrochloric acid were added to a mixture of 2-bromophenylmethanol (34 g, 0.18 mol) and 3,4-dihydro-2H-pyran (18 g, 0.22 mol), and the resulting mixture was stirred overnight at room temperature. The mixture was diluted with diethyl ether, and the organic phase was neutralized with a saturated $NaHCO_3$ aqueous solution. Further, the resultant was dried over anhydrous $MgSO_4$ and was concentrated under reduced pressure to obtain 2-(2-tetrahydro-2H-pyranoxymethyl)bromobenzene, to which dissolved in THF (450 mL) was added a 1.6 M n-BuLi solution in hexane (124 mL, 0.20 mol) at −78° C. over 40 minutes. The resulting solution was stirred for 50 minutes at −78° C., and chlorodimethylsilane (20 g, 0.22 mol) was added thereto. The mixture was warmed gradually at room temperature overnight and then was quenched with water. After evaporation of THF, the residue thereof was extracted with diethylether, and the combined organic layers were washed with brine, and then the resultant was dried over anhydrous $MgSO_4$. The dried resultant was distilled under reduced pressure, thereby obtaining dimethyl[2-(2-tetrahydro-2H-pyranoxymethyl) phenyl]silane (5) (38 g, yield of 83%) as a colorless oil, bp: 135° C. (1.0 mmHg). $^1$H NMR (400 MHz, $CDCl_3$) δ 7.54 (d, J=7.2 Hz, 1H), 7.44 (d, J=7.2 Hz, 1H), 7.40-7.36, (m, 1H), 7.31-7.27 (m, 1H), 4.87 (d, J=12.0 Hz, 1H), 4.74 (s, 1H), 4.60 (d, J=12.0 Hz, 1H), 4.58-4.50 (m, 1H), 4.00-3.95 (m, 1H), 3.62-3.54 (m, 1H), 1.94-1.50 (m, 6H), 0.36 (s, 6H); $^{13}$C NMR (101 MHz, $CDCl_3$) δ 143.6, 136.5, 134.7, 129.4, 128.3, 127.0, 98.1, 69.1, 62.1, 30.6, 25.5, 19.3, −3.0, −3.1; Anal. Calcd for $C_{14}H_{22}O_2Si$; C, 67.15; H, 8.86. Found: C, 67.44; H, 8.91.

Preparation of oxasilacyclopentane (7) from dimethyl[2-(2-tetrahydro-2H-pyranoxymethyl)phenyl]silane (5)

Dimethyl[2-(2-tetrahydro-2H-pyranoxymethyl)phenylsilane (5) (75 g, 0.3 mol) was treated with p-toluenesulfonic acid monohydrate (1.1 g, 6.0 mmol) in MeOH (500 mL) at room temperature for 16 hours. After evaporation of MeOH, the residue thereof was distilled, thereby obtaining oxasilacyclopentane (7) (41 g, yield of 83%) as a colorless oil, bp 45° C. (2.0 mmHg). $^1$H NMR (400 MHz, $CDCl_3$) δ 7.59 (dd, J=7.1, 0.4 Hz, 1H), 7.42-7.37 (m, 1H), 7.33-7.28, (m, 1H), 7.23 (dd, J=7.5, 0.7 Hz, 1H), 5.16 (s, 2H), 0.40 (s, 6H); $^{13}$C NMR (101 MHz, $CDCl_3$) δ 149.7, 135.0, 131.0, 129.5, 126.8, 121.6, 71.5, 0.6; Anal. Calcd for $C_9H_{12}OSi$; C, 65.80; H, 7.36. Found: C, 65.60; H, 7.34.

Preparation of dimethyl(2-(acetoxymethyl)phenyl)silane (12') ($R^2$ and $R^3$: methyl group)

At 0° C., oxasilacyclopentane (7) (1.64 g, 10 mmol) was added to a suspension of $LiAlH_4$ (0.38 g, 10 mmol) in diethyl ether (30 mL), and the resulting mixture was stirred at a room temperature for 100 minutes. Acetyl chloride (7.1 mL, 100 mmol) was added thereto while cooling the mixture at 0° C. The resulting mixture was dried at room temperature overnight, and the dried resultant was filtered through a Florisil and then a silica gel pad. The residue thereof was purified by flash chromatography on silica gel, thereby obtaining dimethyl (2-(acetoxymethyl)phenyl)silane (12') (1.4 g, yield of 67%) as a colorless oil. $R_f$: 0.30 (hexane-ethyl acetate=20:1). $^1$H NMR (400 MHz, $CDCl_3$) δ 7.57 (d, J=7.0 Hz, 1H), 7.42-7.32 (m, 3H), 5.20 (s, 2H), 4.54 (m, 1H), 2.10 (s, 3H), 0.37 (d, J=3.8 Hz, 6H); $^{13}$C NMR (101 MHz, $CDCl_3$) δ 170.8, 140.9, 137.2, 135.0, 129.6, 129.1, 127.8, 66.6, 21.1, −3.1; Anal. Calcd for $C_{11}H_{16}O_2Si$; C, 63.42; H, 7.74. Found: C, 63.48; H, 7.74.

Example 2

Preparation of Silicon-Based Cross-Coupling Reagent

Various kinds of silicon-based cross-coupling reagents were prepared using the compound obtained in Example 1.

Preparation of (E)-(2-(hydroxymethyl)phenyl)dimethyl(1-octenyl)silane: 1a

By platinum-catalyzed hydrosilylation, (E)-(2-(hydroxymethyl)phenyl)dimethyl(1-octenyl)silane: 1a was prepared. At 0° C., a 0.01 M hexane solution of platinum(0)-1, 3-divinyl-1,1,3,3-tetramethyldisiloxane complex (4.0 mL, 40 µmol) and a 10% hexane solution of t-$Bu_3P$ (80 mg, 40 µmol) were added to a solution of dimethyl[2-(2-tetrahydro-2H-pyranoxymethyl)phenylsilane ($R^2$ and $R^3$ in (5): methyl group) (10 g, 40 mmol) and 1-octyne (4.4 g, 40 mmol) in hexane (4 mL).

The resulting mixture was stirred at room temperature for two hours, and filtered with a Celite pad, and the filtrate was concentrated under reduced pressure. The residue thereof was dissolved in MeOH (140 mL), and the resultant was treated with p-toluenesulfonic acid monohydrate (152 mg, 0.80 mmol) at room temperature for four hours. After removal of the solvent under reduced pressure, the residue thereof was purified by flash chromatography on silica gel, thereby obtaining (E)-(2-(hydroxymethyl)phenyl)dimethyl(1-octenyl)silane: 1a (9.0 g, yield of 81%) as a colorless oil, $R_f$: 0.25 (hexane-ethyl acetate=10:1). $^1$H NMR (400 MHz, $CDCl_3$) δ 7.55 (dd, J=7.3, 1.3 Hz, 1H), 7.46 (dd, J=7.5, 0.7 Hz, 1H), 7.40 (td, J=7.5, 1.5 Hz, 1H), 7.28 (td, J=7.3, 1.3 Hz, 1H), 6.15 (dt, J=18.7, 6.4 Hz, 1H), 5.83 (dt, J=18.7, 1.5 Hz, 1H), 4.74 (s, 2H), 2.17-2.12 (m, 2H), 1.42-1.25 (m, 8H), 0.90-0.83 (m, 3H), 0.39 (s, 6H); $^{13}$C NMR (101 MHz, $CDCl_3$) δ 149.7, 146.4, 137.1, 135.1, 130.0, 128.2, 128.0, 127.0, 65.4, 36.8, 31.7, 28.9, 28.5, 22.6, 14.1, −1.2; Anal. Calcd for $C_{17}H_{28}OSi$; C, 73.85; H, 10.21. Found: C, 73.86; H, 10.42.

Preparation of (E)-(2-(hydroxymethyl)phenyl)dimethyl (5-cyano-1-pentenyl)silane: 1b The operation for the preparation of the compound 1a was applied to 1b except that 5-hexynenitrile (0.46 g, 5.0 mmol), 1.3 g and 5.0 mmol of dimethyl[2-(2-tetrahydro-2H-pyranoxymethyl)phenylsilane ($R^2$ and $R^3$ in (5): methyl group) and 1-octyne were employed, thereby obtaining (E)-(2-(hydroxymethyl)phenyl)dimethyl(5-cyano-1-pentenyl)silane: 1b (1.1 g, yield of 84%) as a colorless oil, $R_f$: 0.30 (hexane-ethyl acetate=4:1). $^1$H NMR (400 MHz, $CDCl_3$) δ 7.53 (d, J=7.2 Hz, 1H), 7.46 (d, J=7.2 Hz, 1H), 7.40 (td, J=7.4, 1.2 Hz, 1H), 7.29 (td, J=7.4, 1.2 Hz, 1H), 6.06 (dt, J=18.5, 6.0 Hz, 1H), 5.95 (d, J=18.4 Hz, 1H), 4.73 (s, 2H), 2.36-2.29 (m, 4H), 1.82-1.75 (m, 2H), 0.40 (s, 6H); $^{13}$C NMR (101 MHz, CDCl$_3$) δ 146.4, 145.6, 136.2, 135.0, 131.2, 129.7, 127.7, 126.9, 119.5, 65.1, 35.2, 24.0, 16.4, −1.3; Anal. Calcd for C$_{15}$H$_{21}$NOSi; C, 69.45; H, 8.16. Found: C, 69.68; H, 8.15.

Preparation of (E)-(2-(hydroxymethyl)phenyl)dimethyl(2-phenylethenyl)silane: 1c

The same operation as in the preparation of the compound 1a except that phenylacetylene (0.20 g, 2.0 mmol) was used instead of 0.55 g and 2.2 mmol of dimethyl[2-(2-tetrahydro-2H-pyranoxymethyl)phenylsilane (R$^2$ and R$^3$ in (5): methyl group) and 1-octyne, thereby obtaining (E)-(2-(hydroxymethyl)phenyl) dimethyl(2-phenylethenyl)silane (0.45 g, yield of 84%) as a colorless oil, R$_f$: 0.20 (hexane-ethyl acetate=10: 1). $^1$H NMR (400 MHz, CDCl$_3$) δ 7.62 (dd, J=7.4, 1.3 Hz, 1H), 7.51-7.41 (m, 4H), 7.37-7.27 (m, 4H), 6.97 (d, J=19.2 Hz, 1H), 6.67 (d, J=19.2 Hz, 1H), 4.79 (s, 2H), 0.52 (s, 6H); $^{13}$C NMR (101 MHz, CDCl$_3$) δ 146.5, 145.2, 138.0, 136.4, 135.3, 130.0, 128.6, 128.3, 127.9, 127.8, 127.1, 126.5, 65.4, −1.2; Anal. Calcd for C$_{17}$H$_{20}$Osi; C, 76.07; H, 7.51. Found: C, 75.73; H, 7.55.

Preparation of (E)-(2-(hydroxymethyl)phenyl)dimethyl(4-octene-4-yl)silane: 1f

The same operation as in the production of the compound 1a was carried out except that 4-octyne (0.22 g, 2.0 mmol) was used instead of 0.55 g and 2.2 mmol of dimethyl[2-(2-tetrahydro-2H-pyranoxymethyl)phenylsilane (R$^2$ and R$^3$ in (5): methyl group) and 1-octyne, thereby (E)-(2-(hydroxymethyl)phenyl)dimethyl(4-octene-4-yl)silane (0.45 g, yield of 81%) as a colorless oil. R$_f$: 0.25 (hexane-ethyl acetate=10:1). $^1$H NMR (400 MHz, CDCl$_3$) δ 7.54 (dd, J=7.2, 1.2 Hz, 1H), 7.47 (dd, J=7.2, 1.2 Hz, 1H), 7.40 (td, J=7.3, 1.4 Hz, 1H), 7.29 (m, 1H), 5.80 (t, J=7.2 Hz, 1H), 4.70 (s, 2H), 2.12-2.06 (m, 4H), 1.38 (m, 2H), 1.28-1.18 (m, 2H), 0.90 (t, J=7.4 Hz, 3H), 0.83 (t, J=7.2 Hz, 3H), 0.40 (s, 6H); $^{13}$C NMR (101 MHz, CDCl$_3$) δ 146.6, 142.8, 140.2, 136.7, 135.3, 129.6, 128.0, 126.9, 65.2, 32.1, 30.8, 23.4, 22.6, 14.5, 14.0, −1.2; Anal. Calcd for C$_{17}$H$_{28}$Osi; C, 73.85; H, 10.21. Found: C, 73.67; H, 10.06.

Preparation of (E)-(2-(hydroxymethyl)phenyl)dimethyl(1-octenyl)silane: 1a by using dimethyl(2-(acetoxymethyl)phenyl)silane (12')

At 0° C., a 1.0 M solution of 1-octyne in hexane (0.50 mL, 0.50 mmol) was added dropwise to a mixture of dimethyl(2-(acetoxymethyl)phenyl)silane (12') (104 mg, 0.50 mmol), t-Bu$_3$P (10% hexane solution, 10 mg, 5.0 μmol), and platinum (0)-1,3-divinyl-1,1,3,3-tetramethyldisiloxane complex (0.01 M hexane solution, 0.50 mL, 5.0 μmol). The resulting mixture was stirred at room temperature for four hours, and was filtered through a Florisil pad, and was concentrated under reduced pressure. The residue thereof was dissolved in MeOH (2.5 mL) and water (2.5 mL), and the resultant was treated with K$_2$CO$_3$ (1.4 g, 10 mmol) at 50° C. for 24 hours. The resulting mixture was extracted with diethylether, and the combined organic layers were washed with water and brine, and the washed resultant was dried over anhydrous MgSO$_4$. The residue was purified by flash chromatography on silica gel, thereby obtaining (E)-(2-(hydroxymethyl)phenyl)dimethyl(1-octenyl)silane (113 mg, yield of 82%) as a colorless oil.

Preparation of (2-(hydroxymethyl)phenyl)dimethyl(2-propenyl)silane: 1d

At 0° C., a 0.5 M 2-propenylmagnesium bromide in THF (100 mL, 50 mmol) was added to a solution of oxasilacyclopentane (7) (7.5 g, 46 mmol) in THF, and the resulting mixture was stirred at room temperature for nine hours. The mixture was diluted with diethyl ether and was washed with a saturated NH$_4$Cl aqueous solution, water, and brine. The organic phase was dried over anhydrous MgSO$_4$. After removal of the solvents under reduced pressure, the residue thereof was distilled under reduced pressure, thereby obtaining (2-(hydroxymethyl)phenyl)dimethyl(2-propenyl)silane: 1d (8.4 g, 89%) as a colorless oil, bp 75° C. (0.4 mmHg). $^1$H NMR (400 MHz, CDCl$_3$) δ 7.55 (d, J=7.3, 1.2 Hz, 1H), 7.48 (d, J=7.7 Hz, 1H), 7.42 (dd, J=7.7, 7.3 Hz, 1H), 7.30 (t, J=7.3 Hz, 1H), 5.71 (dq, J=3.1, 1.6 Hz, 1H), 5.37 (dq, J=3.1, 1.3 Hz, 1H), 4.72 (s, 2H), 1.92 (br s, 1H), 1.82 (dd, J=1.6, 1.3 Hz, 3H), 0.44 (s, 6H); $^{13}$C NMR (101 MHz, CDCl$_3$) δ 147.3, 146.6, 135.4, 135.3, 129.7, 126.9, 126.6, 65.1, 22.5, −2.1; Anal. Calcd for C$_{12}$H$_{18}$Osi; C, 69.84; H, 8.79. Found: C, 69.82; H, 8.56.

Preparation of (2-(hydroxymethyl)phenyl)dimethyl(1-phenyletenyl)silane: 1e

At room temperature, a THF (9 mL) solution of oxasilacyclopentane (7) (3.0 g, 19 mmol) was added to a solution of 1-phenylethenylmagnesium bromide in THF (16 mL) [prepared from α-bromostylene (3.7 g, 20 mmol) and Mg (0.50 g, 21 mmol) in accordance with Hopkins, M. H.; Overman, L. E.; Rishton, G. M. J. Am. Chem. Soc. 1991, 113, 5354-5365], and the resulting mixture was stirred at room temperature for two hours, and then the resultant was further stirred at 50° C. for two hours. The resulting mixture was diluted with diethyl ether, and the insoluble material was filtered. The filtrate was washed with a saturated NH$_4$Cl aqueous solution, water, and brine, and then was dried over anhydrous MgSO$_4$. After removal of the solvent under reduced pressure, the residue was purified by flash chromatography on silica gel to obtain (2-(hydroxymethyl)phenyl)dimethyl(1-phenylethenyl)silane: 1e (1.5 g, yield of 30%) as a colorless oil, R$_f$: 0.28 (hexane-ethyl acetate=5:1). $^1$H NMR (400 MHz, CDCl$_3$) δ 7.61 (d, J=7.3 Hz, 1H), 7.48 (d, J=7.5 Hz, 1H), 7.43 (dd, J=7.5, 7.3 Hz, 1H), 7.31 (t, J=7.3 Hz, 1H), 7.25-7.15 (m, 3H), 7.13-7.08 (m, 2H), 6.04 (d, J=1.4 Hz, 1H), 5.71 (d, J=1.4 Hz, 1H), 4.73 (s, 2H), 1.55 (br s, 1H), 0.48 (s, 6H); $^{13}$C NMR (101 MHz, CDCl$_3$) δ 152.0, 146.5, 143.6, 135.8, 135.3, 129.9, 128.8, 128.2, 128.1, 127.1, 126.72, 126.65, 65.2, −0.8; Anal. Calcd for C$_{17}$H$_{20}$Osi; C, 76.07; H, 7.51. Found: C, 76.31; H, 7.48.

Preparation of (2-(hydroxymethyl)phenyl)dimethyl(2-methyl-1-propenyl)silane: 1g

At 0° C., a 0.5 M THF solution of 2-methyl-1-propenylmagnesium bromide (100 mL, 50 mmol) was added to a solution of oxasilacyclopentane (7) (7.5 g, 46 mmol) in THF (50 mL), and the resulting mixture was stirred at room temperature overnight and then was diluted with diethyl ether. The resulting mixture was washed with a saturated NH$_4$Cl aqueous solution, water, and brine, and then was dried over anhydrous MgSO$_4$. The solvent was removed under reduced pressure, and the residue was purified by flash chromatography on neutral aluminum oxide (activity grade III), thereby obtaining (2-(hydroxymethyl)phenyl)dimethyl(2-methyl-1-propenyl)silane: 1g (7.1 g, yield of 71%) as a colorless oil, $R_f$: 0.26 (hexane-ethyl acetate=5:1). $^1$H NMR (400 MHz, $C_6D_6$) δ 7.57 (d, J=7.3 Hz, 1H), 7.45 (d, J=7.7 Hz, 1H), 7.22 (dd, J=7.4, 7.3 Hz, 1H), 7.13 (dd, J=7.7, 7.4 Hz, 1H), 5.41 (s, 1H), 4.63 (d, J=5.9 Hz, 2H), 1.78 (t, J=5.9 Hz, 1H), 1.66 (s, 3H), 1.46 (s, 3H), 0.37 (s, 6H); $^{13}$C NMR (101 MHz, $C_6D_6$) δ 153.4, 147.3, 137.5, 134.9, 129.7, 128.0, 127.0, 123.8, 65.3, 29.3, 23.2, 0.0; Anal. Calcd for $C_{13}H_{20}OSi$; C, 70.85; H, 9.15. Found: C, 70.83; H, 9.23.

Preparation of
[2-(hydroxymethyl)phenyl]dimethyl(vinyl)silane: 1h

At −78° C., a 1.6 M solution of butyllithium (30 mL, 48 mmol) in hexane was added to a solution of 2-bromophenylmethanol (3.7 g, 20 mmol) in THF, and the resulting mixture was stirred at −78° C. for 1.5 hours. At −78° C., chloro (dimethyl)vinylsilane (7.2 g, 60 mmol) was added to the reacted mixture, and the resulting mixture was stirred for two hours. The resulting mixture solution was diluted with diethyl ether, and was washed with water and brine, and then was dried over anhydrous $MgSO_4$. After removal of the solvents under reduced pressure, the residue was purified by flash chromatography on silica gel, thereby obtaining [2-(hydroxymethyl)phenyl]dimethyl(vinyl)silane: 1h (3.1 g, yield of 80%) as a colorless oil, $R_f$: 0.30 (hexane-ethyl acetate=7:1). $^1$H NMR (400 MHz, $CDCl_3$) δ 7.56 (dd, J=7.3, 1.3 Hz, 1H), 7.46 (dd, J=7.1, 0.7 Hz, 1H), 7.41 (td, J=7.4, 1.5 Hz, 1H), 7.30 (td, J=7.3, 1.5 Hz, 1H), 6.39 (dd, J=20.3, 14.6 Hz, 1H), 6.08 (dd, J=14.6, 3.7 Hz, 1H), 5.79 (dd, J=20.3, 3.7 Hz, 1H), 4.74 (s, 2H), 1.71 (br s, 1H), 0.43 (s, 6H); $^{13}$C NMR (101 MHz, $CDCl_3$) δ 146.4, 139.0, 136.2, 135.2, 132.8, 129.8, 128.0, 127.0, 65.3, −1.6; Anal. Calcd for $C_{11}H_{16}OSi$; C, 68.69; H, 8.39. Found: C, 68.43; H, 8.36.

Preparation of [2-(hydroxymethyl)phenyl]dimethyl
(propene-1-yl)silane: 1i, (Z):(E)=94:6

At 0° C., a solution of (Z)-propen-1-ylmagnesium bromide in THF (70 mL) [prepared from (Z)-1-bromo-1-propene (6.0 g, 50 mmol) and Mg (1.71 g, 50 mmol) in accordance with Kant, J., J. Org. Chem. 1993, 58, 2296-2301] was added to a THF solution (20 mL) of oxasilacyclopentane (7) (5.8 g, 35 mmol), and the resulting mixture was stirred at room temperature overnight. The resulting mixture was diluted with diethylether and was filtered to remove unreacted magnesium. The filtrate was washed with a saturated $NH_4Cl$ aqueous solution, water, and brine, and then was dried over anhydrous $MgSO_4$. After removal of the solvents under reduced pressure, the residue was purified by flash chromatography on silica gel, thereby obtaining [2-(hydroxymethyl)phenyl]dimethyl(propene-1-yl)silane: 1i (6.8 g, yield of 94%, (Z): (E)=94:6 as estimated by GC analysis) as a colorless oil, $R_f$: 0.26 (hexane-ethyl acetate=7:1). $^1$H NMR (400 MHz, $CDCl_3$) δ 7.59 (dd, J=7.3, 1.5 Hz, 1H), 7.47 (d, J=7.6 Hz, 1H), 7.41 (td, J=7.5, 1.5 Hz, 1H), 7.29 (td, J=7.3, 1.3 Hz, 1H), 6.52 (dq, J=13.9, 7.0 Hz, 1H), 5.76 (dq, J=13.9, 1.5 Hz, 1H), 4.72 (s, 2H), 1.64 (dd, J=6.8, 1.6 Hz, 3H), 0.45 (s, 6H); $^{13}$C NMR (101 MHz, $CDCl_3$) δ 146.3, 145.1, 137.5, 134.7, 129.7, 129.3, 128.2, 127.0, 65.4, 19.1, −0.2. IR (neat) 3319, 3055, 2961, 2910, 1609, 1435, 1248, 1200, 1124, 1078, 826, 777, 746, 696, 658 cm$^{-1}$. MS (EI, 70 eV) m/z (%) 206 (M$^+$, 0.1), 191 (12), 173 (29), 166 (10), 165 (62), 164 (37), 163 (18), 150 (15), 149 (100), 148 (11), 147 (39), 145 (48), 135 (16), 131 (14), 105 (11), 91 (11), 75 (43), 61 (19); Anal. Calcd for $C_{12}H_{18}OSi$; C, 69.84; H, 8.79. Found: C, 69.82; H, 8.81.

Preparation of
(2-(hydroxylmethyl)phenyl)dimethyl(phenyl)silane:
2a

At −78° C., a 1.0 M solution of phenylmagnesium bromide (65 mL, 65 mmol) in THF was added to a solution of oxasilacyclopentane (7) (9.9 g, 60 mmol) in diethyl ether (250 mL) over 15 minutes, and the resulting mixture was stirred at −78° C. for two hours, and then was stirred at room temperature overnight. The reaction was quenched with a saturated $NH_4Cl$ aqueous solution (40 mL) at 0° C. The aqueous layer was extracted with diethyl ether (2×60 mL), and the combined organic layers were washed with water (2×75 mL) and brine (50 mL), and then was dried over anhydrous $MgSO_4$. After concentration under reduced pressure, the residue was purified by flash chromatography on silica gel, thereby obtaining colorless and solid (2-(hydroxymethyl)phenyl)dimethyl (phenyl)silane: 2a (13.8 g, yield of 95%) as a colorless solid (mp: 53-54° C.), $R_f$: 0.39 (hexane-ethylacetate=4:1). $^1$H NMR (400 MHz, $CDCl_3$) δ 7.59 (d, J=7.6 Hz, 1H), 7.54-7.41 (m, 4H), 7.41-7.29 (m, 4H), 4.54 (s, 2H), 1.38-1.22 (br s, 1H), 0.62 (s, 6H); $^{13}$C NMR (101 MHz, $CDCl_3$) δ 146.5, 139.0, 135.8, 135.5, 133.8, 130.0, 129.2, 128.1, 128.0, 127.0, 65.3, −1.1; Anal. Calcd for $C_{15}H_{18}OSi$; C, 74.33; H, 7.49. Found: C, 74.18; H, 7.52.

Preparation of (2-(hydroxymethyl)phenyl)dimethyl
(4-fluorophenyl)silane: 2b

The same operation as in the production of the compound 2a was carried out except that a 2.0 M $Et_2O$ solution of 4-fluorophenylmagnesium bromide (17 mL, 33 mmol) and oxasilacyclopentane (7) (4.9 g, 30 mmol) were used, thereby obtaining (2-(hydroxymethyl)phenyl)dimethyl(4-fluorophenyl)silane: 2 b (6.8 g, yield of 86%) as a colorless oil, $R_f$: 0.17 (hexane-ethyl acetate=4:1). $^1$H NMR (400 MHz, $CDCl_3$) δ 7.57 (d, J=7.7 Hz, 1H), 7.51-7.41 (m, 4H), 7.32 (td, J=7.0, 1.8 Hz, 1H), 7.08-7.01 (m, 2H), 4.54 (s, 2H), 1.44 (br s, 1H), 0.61 (s, 6H); $^{13}$C NMR (101 MHz, $CDCl_3$) δ 163.7 (d, J=248.4 Hz), 146.5, 135.8 (d, J=7.6 Hz), 135.5, 134.4 (d, J=3.8 Hz), 130.1, 128.0, 127.1, 115.2 (d, J=19.9 Hz), 65.2, −0.9; Anal. Calcd for $C_{15}H_{17}FOSi$; C, 69.19; H, 6.58. Found: C, 69.19; H, 6.58.

Preparation of (2-(hydroxymethyl)phenyl)dimethyl
(2-methylphenyl)silane: 2c

The same operation as in the production of the compound 2a was carried out except that a 2.0 M solution of 2-methylphenylmagnesium bromide in THF (17 mL, 33 mmol) and oxasilacyclopentane (7) (4.9 g, 30 mmol) were used, thereby obtaining (2-(hydroxymethyl)phenyl)dimethyl(2-methylphenyl)silane: 2c (7.6 g, yield of 99%) as a colorless oil, $R_f$: 0.36 (hexane-ethyl acetate=5:1). $^1$H NMR (400 MHz, $CDCl_3$) δ 7.64-7.55 (m, 2H), 7.45-7.39 (m, 2H), 7.35-7.30 (m, 2H), 7.23 (t, J=7.4 Hz, 1H), 7.13 (d, J=7.5 Hz, 1H), 4.46 (s, 2H), 2.17 (s, 3H), 1.34 (br s, 1H), 0.64 (s, 6H); $^{13}$C NMR (101 MHz, $CDCl_3$) δ 146.3, 143.8, 137.0, 136.7, 135.0, 134.6, 130.1, 129.8, 128.3, 127.2, 125.5, 65.2, 22.8, −0.6; Anal. Calcd for $C_{16}H_{20}OSi$; C, 74.95; H, 7.86. Found: C, 75.24; H, 7.94.

Production of (2-(hydroxymethyl)phenyl)dimethyl
(2-thienyl)silane: 2d

At 0° C., a solution of 2-thienylmagnesium bromide in THF (23 mL) [prepared from 2-bromothiophene (5.4 g, 33 mmol) and Mg (0.82 g, 34 mmol) was added to oxasilacyclopentane (7) (4.9 g, 30 mmol) in THF (10 mL) in accordance with Frisell, C.; Lawesson, S.-O. Org. Synth. Coll. Vol. 1972, 5, 642-644], and the resulting mixture was stirred at room temperature for 22 hours. The resulting mixture was diluted with diethylether and was filtered to remove unreacted magnesium. The filtrate was washed with a saturated NH$_4$Cl aqueous solution, water, and brine, and then was dried over anhydrous MgSO$_4$. After removal of the solvents under reduced pressure, the residue was purified by flash chromatography on silica gel, thereby obtaining (2-(hydroxymethyl)phenyl)dimethyl(2-thienyl)silane: 2d (5.9 g, yield of 79%) as a colorless oil, R$_f$: 0.21 (hexane-ethylacetate=5:1). $^1$H NMR (400 MHz, CDCl$_3$) δ 7.64 (d, J=4.6 Hz, 1H), 7.57 (d, J=7.4 Hz, 1H), 7.48 (d, J=7.6 Hz, 1H), 7.44 (t, J=7.4 Hz, 1H), 7.34-7.28 (m, 2H), 7.20 (dd, J=4.6, 3.4 Hz, 1H), 4.64 (s, 2H), 1.47 (s, 1H), 0.68 (s, 6H); $^{13}$C NMR (101 MHz, CDCl$_3$) δ 146.5, 138.5, 135.6, 135.3, 131.3, 130.2, 128.4, 128.2, 127.1, 65.3, 0.2; Anal. Calcd for C$_{13}$H$_{16}$OSSi; C, 62.85; H, 6.49. Found: C, 62.96; H, 6.49.

Preparation of
[2-(hydroxymethyl)phenyl]diisopropylphenylsilane:
2e 2-(2-tetrahydro-2H-pyranoxymethyl)bromobenzene (32 g, 118 mmol) was dissolved in THF (118 ml), and a 1.6M n-BuLi solution in hexane (81 ml, 130 mmol) was slowly added thereto at −78° C., and the resultant solution was stirred at −78° C. for four hours, and then chloro(diisopropyl)silane (21 g, 142 mmol) was added thereto. After stirring the resultant at room temperature for 15 hours, the reaction solution was quenched with a saturated NaHCO$_3$ aqueous solution, and was washed with water three times and with brine once. After drying the resultant over anhydrous MgSO$_4$, the solvent was removed under reduced pressure. The residue thereof was dissolved in MeOH (178 ml), and TsOH.H$_2$O (1.1 g, 6.0 mmol) was added thereto, and the resultant was stirred at room temperature for 18 hours. After concentration, distillation was carried out under reduced pressure, thereby obtaining oxasilacyclopentane (24.3 g, 93%) as a clear and colorless liquid.

The resultant oxasilacyclopentane (11.0 g, 50.0 mmol) was dissolved in THF (125 ml), and a 1.07M solution of phenylmagnesium bromide in THF (51 ml, 55 mmol) was slowly added thereto at 0° C. After finishing dropping the solution, the resultant was stirred at room temperature for 16 hours. The reaction solution was diluted with diethyl ether and was washed with a saturated NH$_4$Cl aqueous solution, water, and brine, and then was dried over anhydrous MgSO$_4$. After removal of the solvents, the residue was purified by column chromatography on silica gel, thereby obtaining [2-(hydroxymethyl)phenyl]diisopropylphenylsilane (13.5 g, 90%) as colorless crystal.

Example 3

Preparation of Organic Compound by Using
Silicon-Based Cross-Coupling Reagents 1a to 1i of
the Present Invention The silicon-based cross-coupling reagents 1a to 1i of the present invention were used to carry out cross coupling reaction with an organic halide I—R$^{10}$, thereby preparing various kinds of organic compounds. Table 1 shows reaction times, yields, a silicon-based cross-coupling reagent R$^1$ used and an organic halide R$^{10}$. Note that, in Table 1, product numbers correspond to the numbers of the following substances respectively.

TABLE 1

| Product | R$^1$ | R$^{10}$ | Reaction time (h) | Yield (%) |
|---|---|---|---|---|
| p1 | (E)-HexCH=CH | 4-NC—C$_6$H$_4$ | 20 | 93 |
| p2 | (E)-HexCH=CH | 4-EtO$_2$C—C$_6$H$_4$ | 18 | 96 |
| p3 | (E)-HexCH=CH | 4-Me(O)C—C$_6$H$_4$ | 17 | 94 |
| p4 | (E)-HexCH=CH | 4-H(O)C—C$_6$H$_4$ | 20 | 94 |
| p5 | (E)-HexCH=CH | 4-O$_2$N—C$_6$H$_4$ | 26 | 99 |
| p6 | (E)-HexCH=CH | 4-Cl—C$_6$H$_4$ | 19 | 93 |
| p7 | (E)-HexCH=CH | 4-MeO—C$_6$H$_4$ | 40 | 89 |
| p8 | (E)-HexCH=CH | 3-t-BuMe$_2$SiOCH$_2$—C$_6$H$_4$ | 23 | 98 |
| p9 | (E)-HexCH=CH | 3-HOCH$_2$—C$_6$H$_4$ | 47 | 88 |
| p10 | (E)-HexCH=CH | 2-Me-C$_6$H$_4$ | 47 | 94 |
| p11 | (E)-HexCH=CH | 1-naphthyl | 23 | 91 |
| p12 | (E)-HexCH=CH | 3-pirydyl | 23 | 80 |
| p13 | (E)-HexCH=CH | 2-thienyl | 23 | 99 |
| p14 | (E)-NC(CH$_2$)$_3$CH=CH | 4-EtO$_2$C—C$_6$H$_4$ | 19 | 95 |
| p15 | (E)-PhCH=CH | 4-EtO$_2$C—C$_6$H$_4$ | 19 | 88 |
| p16 | H$_2$C=CMe | 4-EtO$_2$C—C$_6$H$_4$ | 24 | 96 |
| p17 | H$_2$C=CPh | 4-EtO$_2$C—C$_6$H$_4$ | 25 | 95 |
| p18 | H$_2$C=CPh | 4-MeO—C$_6$H$_4$ | 12 | 80 |
| p19 | (E)-PrCH=CPr | 4-EtO$_2$C—C$_6$H$_4$ | 29 | 92 |
| p20 | Me$_2$C=CH | 4-EtO$_2$C—C$_6$H$_4$ | 25 | 96 |
| p21 | (E)-NC(CH$_2$)$_3$CH=CH | (E)-HexCH=CH | 3 | 73 |
| p22 | (E)-NC(CH$_2$)$_3$CH=CH | (Z)-HexCH=CH | 2 | 78 |
| p23 | H$_2$C=CH | 4-EtO$_2$C—C$_6$H$_4$ | 19 | 87 |
| p24 | (Z)-MeCH=CH | 4-EtO$_2$C—C$_6$H$_4$ | 19 | 91 |

Any one of the silicon-based cross-coupling reagents 1a to 1i (1.1 mmol) and the organic halide (1.0 mmol) were sequentially added to a mixture of K$_2$CO$_3$ (304 mg, 2.2 mmol), tri-2-furilic phosphine (4.6 mg, 20 μmol), and PdCl$_2$ (1.8 mg, 10 μmol) in DMSO (2.5 mL), and the resulting mixture was stirred at 35° C. When each of the times shown in Table 1 had passed, the resulting mixture was diluted with diethyl ether and was washed with water and brine, and then was dried over anhydrous MgSO$_4$. After concentration under reduced pressure, the residue was purified by flash chromatography on silica gel, thereby obtaining organic compounds p1 to p24 which were cross-coupling products respectively corresponding to yields shown in Table 1. The following shows chemical formulas and characteristic data of the resultant organic compounds p1 to p22 and p24.
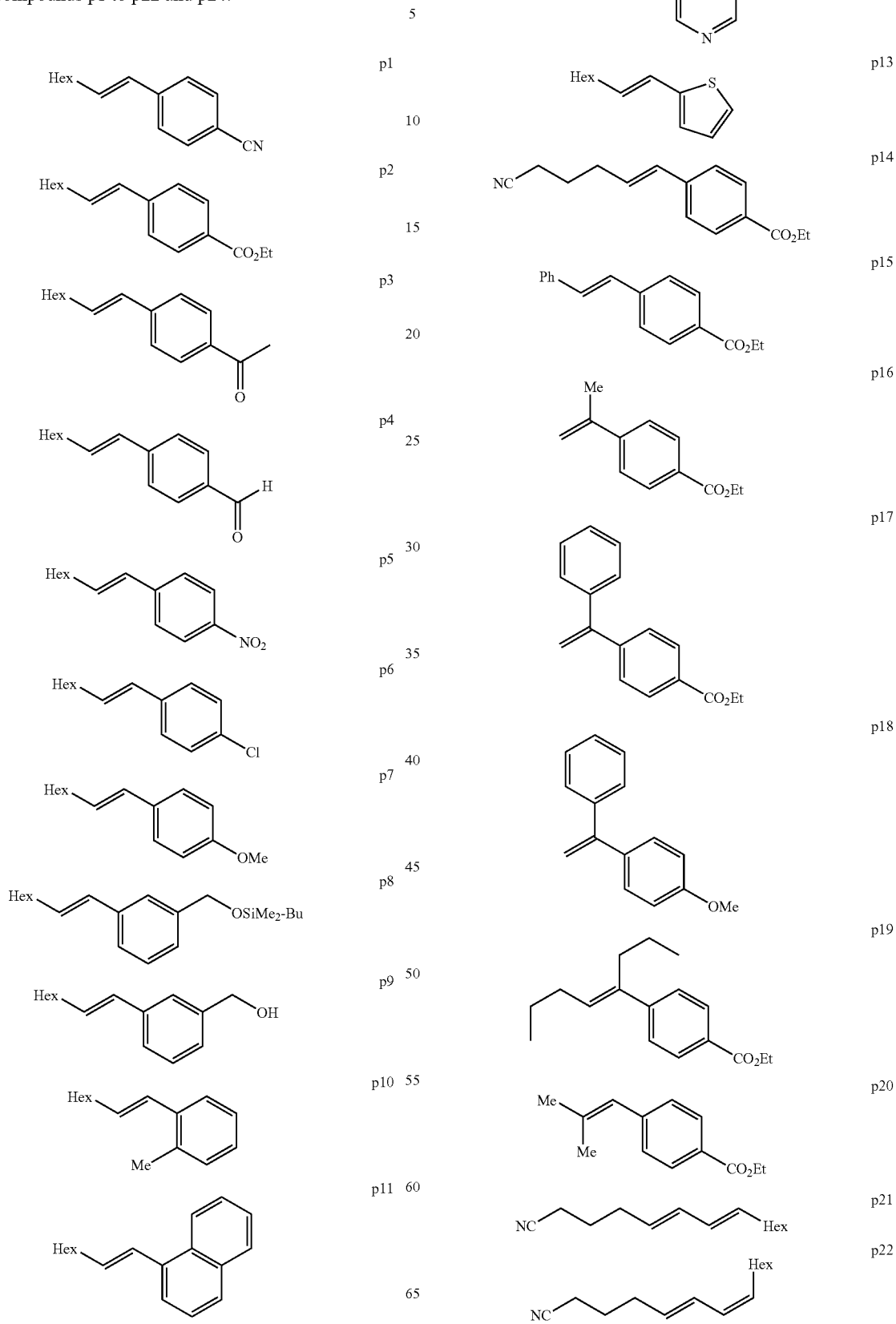

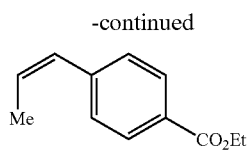

p24

(E)-1-(4-cyanophenyl)-1-octene: p1

A colorless oil, $R_f$: 0.31 (hexane-ethyl acetate=20:1). $^1$H NMR (400 MHz, CDCl$_3$) δ 7.55 (d, J=8.4 Hz, 2H), 7.39 (d, J=8.4 Hz, 2H), 6.38-6.35 (m, 2H), 2.24-2.20 (m, 2H), 1.50-1.42 (m, 2H), 1.40-1.25 (m, 6H), 0.92-0.86 (m, 3H); $^{13}$C NMR (101 MHz, CDCl$_3$) δ 142.4, 135.5, 132.2, 128.3, 126.3, 119.1, 109.8, 33.1, 31.6, 28.9, 28.8, 22.5, 14.0; Anal. Calcd for C$_{15}$H$_{19}$N; C, 84.46; H, 8.98. Found: 84.37; H, 8.96.

(E)-4-(1-octenyl)ethyl benzoate: p2

A colorless oil, $R_f$: 0.40 (hexane-ethyl acetate=20:1). $^1$H NMR (400 MHz, CDCl$_3$) δ 7.96 (d, J=7.0 Hz, 2H), 7.38 (d, J=7.0 Hz, 2H), 6.45-6.32 (m, 2H), 4.37 (q, J=7.2 Hz, 2H), 2.23 (q, J=7.2 Hz, 2H), 1.53-1.28 (m, 11H), 0.94-0.86 (m, 3H); $^{13}$C NMR (101 MHz, CDCl$_3$) δ 166.5, 142.4, 134.2, 129.8, 129.0, 128.5, 125.7, 60.8, 33.2, 31.7, 29.1, 28.9, 22.6, 14.3, 14.1; Anal. Calcd for C$_{17}$H$_{24}$O$_2$; C, 78.42; H, 9.29. Found: C, 78.45; H, 9.41.

(E)-1-(4-acetylphenyl)-1-octene: p3

A colorless oil, $R_f$: 0.30 (hexane-ethyl acetate=20:1). $^1$H NMR (400 MHz, CDCl$_3$) δ 7.88 (d, J=8.4 Hz, 2H), 7.39 (d, J=8.4 Hz, 2H), 6.43-6.33 (m, 2H), 2.57 (s, 3H), 2.23 (q, J=6.4 Hz, 2H), 1.52-1.42 (m, 2H), 1.40-1.25 (m, 6H), 0.92-0.86 (m, 3H); $^{13}$C NMR (101 MHz, CDCl$_3$) δ 197.5, 142.6, 135.3, 134.5, 128.8, 128.7, 125.8, 33.1, 31.7, 29.1, 28.9, 26.5, 22.6, 14.0; Anal. Calcd for C$_{16}$H$_{22}$O; C, 83.43; H, 9.63. Found: C, 83.72; H, 9.74.

(E)-1-(4-formylphenyl)-1-octene: p4

A colorless oil, $R_f$: 0.30 (hexane-ethyl acetate=30:1). $^1$H NMR (400 MHz, CDCl$_3$) δ 9.96 (s, 1H), 7.80 (d, J=8.4 Hz, 2H), 7.48 (d, J=8.4 Hz, 2H), 6.64-6.42 (m, 2H), 2.28-2.22 (m, 2H), 1.53-1.44 (m, 2H), 1.40-1.25 (m, 6H), 0.92-0.86 (m, 3H); $^{13}$C NMR (101 MHz, CDCl$_3$) δ 191.7, 144.1, 135.4, 134.8, 130.1, 128.9, 126.3, 33.2, 31.7, 29.0, 28.9, 22.6, 14.1; Anal. Calcd for C$_{15}$H$_{20}$O; C, 83.28; H, 9.32. Found: C, 83.40; H, 9.37.

(E)-1-(4-nitrophenyl)-1-octene: p5

A colorless oil, $R_f$: 0.17 (hexane-ethyl acetate=30:1). $^1$H NMR (400 MHz, CDCl$_3$) δ 8.14 (d, J=8.8 Hz, 2H), 7.44 (d, J=8.8 Hz, 2H), 6.46-6.42 (m, 2H), 2.30-2.20 (m, 2H), 1.54-1.42 (m, 2H), 1.40-1.24 (m, 6H), 0.93-0.87 (m, 3H); $^{13}$C NMR (101 MHz, CDCl$_3$) δ 146.3, 144.4, 136.7, 128.0, 126.3, 123.9, 33.2, 31.6, 28.91, 28.87, 22.6, 14.0; HRMS (FAB+) Calcd for C$_{14}$H$_{20}$NO$_2$: [M+H]+, 234.1494. Found: m/z 234.1497.

(E)-1-(4-chlorophenyl)-1-octene: p6

A colorless oil, $R_f$: 0.60 (hexane). $^1$H NMR (400 MHz, CDCl$_3$) δ 7.26 (s, 4H), 6.33 (dt, J=15.5, 1.2 Hz, 1H), 6.21 (dt, J=15.5, 6.8 Hz, 1H), 2.20 (q, J=6.8 Hz, 2H), 1.52-1.42 (m, 2H), 1.40-1.23 (m, 6H), 0.94-0.88 (m, 3H); $^{13}$C NMR (101 MHz, CDCl$_3$) δ 136.4, 132.2, 132.0, 128.54, 128.49, 127.1, 33.0, 31.7, 29.2, 28.9, 22.6, 14.1; HRMS (EI): Calcd for C$_{14}$H$_{19}$Cl; M+, 222.1175. Found: m/z 222.1172.

(E)-1-(4-methoxyphenyl)-1-octene: p7

A colorless oil, $R_f$: 0.36 (hexane-ethyl acetate=50:1). $^1$H NMR (400 MHz, CDCl$_3$) δ 7.28 (d, J=8.7 Hz, 2H), 6.84 (d, J=8.7 Hz, 2H), 6.33 (d, J=15.7 Hz, 1H), 6.09 (dt, J=15.7, 7.0 Hz, 1H), 3.81 (s, 3H), 2.19 (q, J=7.5 Hz, 2H), 1.50-1.42 (m, 2H), 1.40-1.26 (m, 6H), 0.93-0.88 (m, 3H); $^{13}$C NMR (101 MHz, CDCl$_3$) δ 158.6, 130.8, 129.1, 129.0, 126.9, 113.9, 55.2, 33.0, 31.8, 29.5, 28.9, 22.6, 14.1; Anal. Calcd for C$_{15}$H$_{22}$O; C, 82.52; H, 10.16. Found: C, 82.52; H, 9.98.

(E)-1-(3-(tert-butyldimethylsyloxymethyl)phenyl)-1-octene: p8

A colorless oil. $R_f$: 0.35 (hexane-ethyl acetate=50:1). $^1$H NMR (400 MHz, CDCl$_3$) δ 7.30 (s, 1H), 7.25-7.13 (m, 3H), 6.37 (d, J=15.7 Hz, 1H), 6.22 (dt, J=15.7, 6.9 Hz, 1H), 4.72 (s, 2H), 2.20 (q, J=7.7 Hz, 2H), 1.50-1.42 (m, 2H), 1.38-1.26 (m, 6H), 0.95 (s, 9H), 0.39 (t, J=6.9 Hz, 3H), 0.10 (s, 6H); $^{13}$C NMR (101 MHz, CDCl$_3$) δ 141.5, 137.8, 131.2, 129.7, 128.3, 124.49, 124.47, 123.5, 64.9, 33.0, 31.7, 29.3, 28.9, 26.0, 22.6, 18.4, 14.1, −5.2; Anal. Calcd for C$_{21}$H$_{36}$Osi; C, 75.84; H, 10.91. Found: C, 75.97; H, 11.13.

(E)-1-(~3-(hydroxymethyl)phenyl)-1-octene: p9

A colorless oil, $R_f$: 0.30 (hexane-ethyl acetate=5:1). $^1$H NMR (400 MHz, CDCl$_3$) δ 7.36 (s, 1H), 7.32-7.27 (m, 2H), 7.21-7.18 (m, 1H), 6.38 (d, J=15.6 Hz, 1H), 6.26 (dt, J=16.0, 6.8 Hz, 1H), 4.68 (s, 2H), 2.21 (q, J=7.2 Hz, 2H), 1.51-1.42 (m, 2H), 1.40-1.26 (m, 6H), 0.93-0.87 (m, 3H); $^{13}$C NMR (101 MHz, CDCl$_3$) δ 141.0, 138.3, 131.7, 129.4, 128.7, 125.35, 125.32, 124.4, 65.4, 33.0, 31.7, 29.3, 28.9, 22.6, 14.1; Anal. Calcd for C$_{15}$H$_{22}$O; C, 82.52; H, 10.16. Found: C, 82.63; H, 10.40.

(E)-1-(2-(methylphenyl)-1-octene: p10

A colorless oil, $R_f$: 0.71 (hexane). $^1$H NMR (400 MHz, CDCl$_3$) δ 7.41 (d, J=7.2 Hz, 1H), 7.19-7.10 (m, 3H), 6.57 (d, J=15.6 Hz, 1H), 6.10 (dt, J=15.6, 6.8 Hz, 1H), 2.34 (s, 3H), 2.23 (q, J=7.2 Hz, 2H), 1.54-1.42 (m, 2H), 1.40-1.26 (m, 6H), 0.92-0.88 (m, 3H); $^{13}$C NMR (101 MHz, CDCl$_3$) δ 137.1, 134.8, 132.6, 130.1, 127.5, 126.7, 126.0, 125.4, 33.3, 31.7, 29.4, 28.9, 22.6, 19.8, 14.1; Anal. Calcd for C$_{15}$H$_{22}$; C, 89.04; H, 10.96. Found: C, 88.97; H, 11.18.

(E)-1-(3-(hydroxymethyl)phenyl)-1-octene: p11

A colorless oil, $R_f$: 0.50 (hexane). $^1$H NMR (400 MHz, CDCl$_3$) δ 8.13 (d, J=7.6 Hz, 1H), 7.84 (d, J=7.2 Hz, 1H), 7.74 (d, J=8.0 Hz, 1H), 7.58-7.40 (m, 4H), 7.11 (d, J=15.2 Hz, 1H), 6.24 (dt, J=16.0, 7.2 Hz, 1H), 2.33 (q, J=7.6 Hz, 2H), 1.60-1.52 (m, 2H), 1.46-1.32 (m, 6H), 0.94-0.88 (m, 3H); $^{13}$C NMR (101 MHz, CDCl$_3$) δ 135.8, 134.6, 133.6, 131.1, 128.4, 127.1, 126.8, 125.74, 125.65, 125.58, 124.0, 123.5, 33.5, 31.8, 29.4, 29.0, 22.7, 14.1; Anal. Calcd for C$_{18}$H$_{22}$; C, 90.70; H, 9.30. Found: C, 90.61; H, 9.32.

(E)-1-(3-pyridyl)-1-octene: p12

A colorless oil, $R_f$: 0.35 (hexane-ethyl acetate=5:1). $^1$H NMR (400 MHz, CDCl$_3$) δ 8.56 (s, 1H), 8.42 (d, J=3.7 Hz, 1H), 7.65 (d, J=7.9 Hz, 1H), 7.22 (dd, J=7.8, 4.8 Hz, 1H), 6.38-6.26 (m, 2H), 2.26-2.20 (m, 2H), 1.52-1.43 (m, 2H), 1.40-1.26 (m, 6H), 0.92-0.86 (m, 3H); $^{13}$C NMR (101 MHz, CDCl$_3$) δ 147.8, 147.7, 133.8, 133.5, 132.5, 126.1, 123.4, 33.1, 31.7, 29.1, 28.9, 22.6, 14.1; Anal. Calcd for C$_{13}$H$_{19}$N; C, 82.48; H, 10.12. Found: C, 82.20; H, 10.06.

(E)-1-(2-thienyl)-1-octene: p13

A colorless oil, R$_f$: 0.70 (hexane). $^1$H NMR (400 MHz, CDCl$_3$) δ 7.08 (d, J=5.2 Hz, 1H), 6.95-6.91 (m, 1H), 6.86 (d, J=3.2 Hz, 1H), 6.50 (d, J=15.6 Hz, 1H), 6.07 (dt, J=15.6, 6.8 Hz, 1H), 2.17 (q, J=7.2 Hz, 2H), 1.52-1.41 (m, 2H), 1.40-1.24 (m, 6H), 0.94-0.86 (m, 3H); $^{13}$C NMR (101 MHz, CDCl$_3$) δ 131.3, 127.2, 124.1, 123.0, 122.9, 108.2, 32.9, 31.7, 29.2, 28.9, 22.6, 14.1. HRMS (EI) Calcd for Cl$_2$H$_{18}$S; M+, 194.1129. Found: m/z 194.1126.

(E)-6-4-(5-cyano-1-pentenyl)ethylbenzoate: p14

A colorless oil, R$_f$: 0.30 (hexane-ethyl acetate=5:1). $^1$H NMR (400 MHz, CDCl$_3$) δ 7.98 (d, J=6.4 Hz, 2H), 7.39 (d, J=6.8 Hz, 2H), 6.50 (d, J=16.0 Hz, 1H), 6.31-6.22 (m, 1H), 4.36 (q, J=7.2 Hz, 2H), 2.44-2.38 (m, 4H), 1.86 (m, 4H), 1.39 (t, J=7.2 Hz, 3H); $^{13}$C NMR (101 MHz, CDCl$_3$) δ 166.4, 141.4, 131.2, 130.4, 129.9, 129.1, 125.9, 119.4, 60.9, 31.7, 24.8, 16.5, 14.3. HRMS (EI) Calcd for C$_{15}$H$_{17}$NO$_2$; M+, 243.1259. Found: m/z 243.1259.

(E)-4-(2-phenylethenyl)ethylbenzoate: p15

A colorless solid, (mp 106.0-106.5° C.), R$_f$: 0.30 (hexane-ethyl acetate=20:1). $^1$H NMR (400 MHz, CDCl$_3$) δ 8.03 (d, J=8.4 Hz, 2H), 7.58-7.52 (m, 4H), 7.41-7.36 (m, 2H), 7.32-7.27 (m, 1H), 7.22 (d, J=16.4 Hz, 1H), 7.13 (d, J=16.4 Hz, 1H), 4.39 (q, J=7.1 Hz, 2H), 1.41 (t, J=7.1 Hz, 3H); $^{13}$C NMR (101 MHz, CDCl$_3$) δ 166.4, 141.7, 136.7, 131.1, 130.0, 129.2, 128.8, 128.2, 127.6, 126.8, 126.3, 60.9, 14.4; Anal. Calcd for C$_{17}$H$_{16}$O$_2$; C, 80.93; H, 6.39. Found: C, 81.18; H, 6.27.

4-(propene-2-yl)ethylbenzoate: p16

A colorless oil, R$_f$: 0.40 (hexane-ethyl acetate=10:1). $^1$H NMR (400 MHz, CDCl$_3$) δ 8.00 (dd, J=8.0 Hz, 2H), 7.52 (d, J=8.2 Hz, 2H), 5.47 (dq, J=1.3, 0.7 Hz, 1H), 5.19 (qd, J=1.5, 1.3 Hz, 1H), 4.38 (q, J=7.1 Hz, 2H), 2.17 (dd, J=1.5, 0.7 Hz, 3H), 1.40 (t, J=7.1 Hz, 3H); $^{13}$C NMR (101 MHz, CDCl$_3$) δ 166.7, 145.8, 142.7, 129.8, 129.5, 125.6, 114.7, 61.1, 21.9, 14.6. HRMS (FAB+) Calcd for C$_{12}$H$_{14}$O$_2$; M+, 190.0994. Found: m/z 190.0993.

4-(1-phenyletenyl)ethylbenzoate: p17

A colorless solid (mp 46.7-47.3° C.), R$_f$: 0.33 (hexane-ethyl acetate=10:1). $^1$H NMR (400 MHz, CDCl$_3$) δ 8.02 (d, J=8.6 Hz, 2H), 7.41 (d, J=8.6 Hz, 2H), 7.36-7.30 (m, 5H), 5.55 (d, J=1.1 Hz, 1H), 5.54 (d, J=1.1 Hz, 1H), 4.39 (q, J=7.1 Hz, 2H), 1.41 (t, J=7.1 Hz, 3H); $^{13}$C NMR (101 MHz, CDCl$_3$) δ 164.4, 149.3, 145.9, 140.8, 129.7, 129.5, 128.3, 128.2, 128.0, 115.8, 60.9, 14.3; Anal. Calcd for C$_{17}$H$_{16}$O$_2$; C, 80.93; H, 6.39. Found: C, 81.01; H, 6.47.

1-(4-methoxyphenyl)-1-phenylethene: p18

A colorless solid (mp 75.3-76.8° C.), R$_f$: 0.39 (hexane-ethyl acetate=15:1). $^1$H NMR (400 MHz, CDCl$_3$) δ 7.38-7.31 (m, 5H), 7.28 (d, J=8.8 Hz, 2H), 6.87 (d, J=8.8 Hz, 2H), 5.41 (d, J=1.4 Hz, 1H), 5.36 (d, J=1.4 Hz, 1H), 3.83 (s, 3H); $^{13}$C NMR (101 MHz, CDCl$_3$) δ 159.6, 149.7, 142.0, 134.2, 129.6, 128.6, 128.4, 127.9, 113.7, 113.2, 55.5; Anal. Calcd for C$_{15}$H$_{14}$O; C, 85.68; H, 6.71. Found: C, 85.67; H, 6.73.

(E)-4-(4-octene-4-yl)ethylbenzoate: p19

A colorless oil, R$_f$: 0.40 (hexane-ethyl acetate=30:1). $^1$H NMR (400 MHz, CDCl$_3$) δ 7.97 (d, J=8.6 Hz, 2H), 7.39 (d, J=8.8 Hz, 2H), 5.76 (t, J=7.3 Hz, 1H), 4.37 (q, J=7.1 Hz, 2H), 2.49 (t, J=7.5 Hz, 2H), 2.19 (q, J=7.3 Hz, 2H), 1.53-1.42 (m, 2H), 1.41-1.32 (m, 5H), 0.97 (t, J=7.3 Hz, 3H), 0.88 (t, J=7.3 Hz, 3H); $^{13}$C NMR (101 MHz, CDCl$_3$) δ 166.6, 148.0, 139.4, 131.1, 129.5, 128.4, 126.2, 60.8, 31.4, 30.7, 22.9, 21.8, 14.4, 14.0, 13.9; Anal. Calcd for C$_{17}$H$_{24}$O$_2$; C, 78.42; H, 9.29. Found: C, 78.28; H, 9.14.

4-(2-methylpropenyl)ethylbenzoate: p20

A colorless oil, R$_f$: 0.38 (hexane-ethyl acetate=10:1). $^1$H NMR (400 MHz, CDCl$_3$) δ 7.98 (d, J=8.3 Hz, 2H), 7.28 (d, J=8.3 Hz, 2H), 6.29 (s, 1H), 4.37 (q, J=7.1 Hz, 2H), 1.93 (s, 3H), 1.88 (s, 3H), 1.39 (t, J=7.1 Hz, 3H); $^{13}$C NMR (101 MHz, CDCl$_3$) δ 166.6, 143.3, 137.9, 129.3, 128.5, 127.7, 124.6, 60.8, 27.1, 19.6, 14.3; Anal. Calcd for C$_{13}$H$_{16}$O$_2$; C, 76.44; H, 7.90. Found: C, 76.24; H, 7.99.

(5E,7E)-tetradeca-5,7-dienenitryl: p21

A colorless oil, R$_f$: 0.42 (hexane-ethyl acetate=5:1). $^1$H NMR (400 MHz, CDCl$_3$) δ 6.11-5.94 (m, 2H), 5.63 (dt, J=14.6, 7.0 Hz, 1H), 5.46 (dt, J=14.8, 7.0 Hz, 1H), 2.34 (t, J=7.1 Hz, 2H), 2.22 (q, J=7.1 Hz, 2H), 2.06 (dt, J=7.1, 7.0 Hz, 2H), 1.80-1.71 (m, 2H), 1.45-1.20 (m, 8H), 0.88 (t, J=7.0 Hz, 3H); $^{13}$C NMR (101 MHz, CDCl$_3$) δ 134.1, 132.6, 129.6, 128.5, 119.6, 32.6, 31.7, 31.2, 29.2, 28.9, 25.0, 22.6, 16.3, 14.1; Anal. Calcd for C$_{14}$H$_{23}$N; C, 81.89; H, 11.29. Found: C, 82.18; H, 11.56.

(5E,7Z)-tetradeca-5,7-dienenitryl: p22

A colorless oil, R$_f$: 0.36 (hexane-ethyl acetate=7:1). $^1$H NMR (400 MHz, CDCl$_3$) δ 6.37 (dd, J=15.1, 10.9 Hz, 1H), 5.94 (t, J=10.9 Hz, 1H), 5.55 (dt, J=15.0, 7.6 Hz, 1H), 5.37 (dt, J=10.9, 7.6 Hz, 1H), 2.35 (t, J=7.1 Hz, 2H), 2.27 (m, 2H), 2.16 (m, 2H), 1.77 (m, 2H), 1.41-1.21 (m, 8H), 0.88 (t, J=6.9 Hz, 3H); $^{13}$C NMR (101 MHz, CDCl$_3$) δ 131.7, 130.8, 127.84, 127.81, 119.6, 31.7, 31.5, 29.6, 28.9, 27.7, 25.0, 22.6, 16.4, 14.1; Anal. Calcd for C$_{14}$H$_{23}$N; C, 81.89; H, 11.29. Found: C, 82.19; H, 11.18.

4-(propene-1-yl)ethylbenzoate[(Z):(E)=94.6]: p24

A colorless oil, R$_f$: 0.33 (hexane-ethyl acetate=20:1). $^1$H NMR (400 MHz, CDCl$_3$) δ 8.01 (dd, J=8.4 Hz, 2H), 7.35 (d, J=8.2 Hz, 2H), 6.46 (dd, J=11.8, 1.8 Hz, 1H), 5.90 (dq, J=11.8, 7.2 Hz, 1H), 4.38 (q, J=7.2 Hz, 2H), 1.91 (dd, J=7.2, 1.8 Hz, 3H), 1.40 (t, J=7.2 Hz, 3H); $^{13}$C NMR (101 MHz, CDCl$_3$) δ 166.5, 142.2, 129.4, 129.1, 129.0, 128.7, 128.3, 60.8, 14.8, 14.3. IR (neat) 2980, 1715, 1609, 1367, 1310, 1277, 1178, 1105, 1020, 866, 773, 733, 721, 700 cm$^{-1}$. MS (EI, 70 eV) m/z (%) 190 (M$^+$, 50), 162 (12), 146 (13), 145 (100), 117 (20), 115 (25), 91 (10); Anal. Calcd for C$_{12}$H$_{14}$O$_2$; C, 75.76; H, 7.42. Found: C, 75.90; H, 7.44.

Example 4

Gram-Scale Cross-Coupling Reaction

The silicon-based cross-coupling reagent 1a (9.1 g, 33 mmol) of the present invention and 4-ethyl iodobenzoate (8.3 g, 30 mmol) were sequentially added to a mixture of $K_2CO_3$ (9.1 g, 66 mmol), tri(2-furyl)phosphine (138 mg, 0.60 mmol), and $PdCl_2$ (54 mg, 0.30 mmol) in DMSO (75 mL), and the resulting mixture was stirred at 35° C. for 21 hours. The resulting mixture was diluted with diethyl ether, and was washed with water and brine, and then was dried over anhydrous $MgSO_4$. The resultant was concentrated under reduced pressure and then was distilled under reduced pressure (1.0 mmHg), thereby obtaining cyclic silyl ether (corresponding to the aforementioned formula (11)) (3.1 g, 62%). The residue thereof was further purified by flash chromatography on silica gel, thereby obtaining (E)-1-(4-ethoxycarbonylphenyl)-1-octene (7.6 g, 97%).

The cyclic silyl ether (11) obtained as a by-product was reacted with acetyl chloride in the presence of reducer such as lithium aluminum hydride, thereby obtaining dimethyl(2-(acetoxymethyl)phenyl)silane (12) (yield of 67%). The resultant dimethyl (2-(acetoxymethyl)phenyl)silane (12) was reacted with 1-octyne in the presence of the platinum catalyst, thereby reproducing the silicon-based cross-coupling reagent 1a (yield of 85%).

Example 5

Method for Preparing Organic Compounds by Using Silicon-Based Cross-Coupling Reagents 2a to 2d of the Present Invention Any one of the silicon-based cross-coupling reagents 2a to 2d of the present invention was used to carry out cross-coupling reaction with an organic halide I—$R^{10}$, thereby producing various kinds of organic compounds. Table 2 shows reaction times, yields, the silicon-based cross-coupling reagent $R^1$ used and $R^{10}$ of an organic halide I—$R^{10}$. Note that, in Table 2, products are numbered to correspond to numbers of the following substances respectively.

TABLE 2

| Product | $R^1$ | $R^{10}$ | Reaction time (h) | Yield (%) |
|---|---|---|---|---|
| P31 | Ph | 4-NC—$C_6H_4$ | 7 | 97 |
| P32 | Ph | 4-MeO—$C_6H_4$ | 16 | 99 |
| P33 | Ph | 2,6-$Me_2$-$C_6H_4$ | 13 | 94 |
| P34 | Ph | 3-pirydyl | 13 | 96 |
| P35 | Ph | 2-thyenyl | 13 | 93 |
| P36 | 4-F—$C_6H_4$ | 4-$EtO_2$C—$C_6H_4$ | 3 | 91 |
| P37 | 2-Me-$C_6H_4$ | 4-$EtO_2$C—$C_6H_4$ | 5 | 81 |
| P38 | 2-thyenyl | 4-$EtO_2$C—$C_6H_4$ | 10 | 93 |
| P39 | Ph | 4-$F_3$C—$C_6H_4$ | 16 | 97 |
| P40 | Ph | 4-Me(O)C—$C_6H_4$ | 13 | 95 |
| P41 | Ph | 4-H(O)C—$C_6H_4$ | 27 | 96 |
| P42 | Ph | 4-$EtO_2$C—$C_6H_4$ | 10 | 84 |
| P43 | Ph | 4-$O_2$N—$C_6H_4$ | 13 | 97 |
| P44 | Ph | 4-Cl—$C_6H_4$ | 13 | 98 |
| P45 | Ph | 2-t-$BuMe_2SiOCH_2$—$C_6H_4$ | 13 | 95 |
| P46 | Ph | 2-$HOCH_2$—$C_6H_4$ | 13 | 91 |
| P47 | Ph | 1-naphthyl | 13 | 98 |
| P48 | Ph | 2-pyradyl | 13 | 92 |
| P49 | Ph | (E)-BuCH=CH | 13 | 83 |
| P50 | Ph | (Z)-HexCH=CH | 13 | 85 |

An aryl iodide (0.7 mmol) and water (25 mg, 1.4 mmol) were sequentially added to a mixture of an arylsilane (0.81 mmol), $K_2CO_3$ (194 mg, 1.4 mmol), N-(2-diphenylphosphinobenzyliden)cyclohexylamine (10.4 mg, 28 μmol), and $PdCl_2$ (3.7 mg, 21 μmol) in DMSO (4.0 mL), and the resulting mixture was stirred at 50° C. When each of the times shown in Table 2 had passed, the resulting mixture was diluted with diethyl ether and was washed with water and brine, and then was dried over anhydrous $MgSO_4$. After concentration under reduced pressure, the residue was purified by flash chromatography on silica gel to obtain organic compounds p31 to p50 which were cross-coupling products respectively corresponding to yields shown in Table 2. The following shows chemical formulas and analysis data of the resultant organic compounds p36, p37, and p38.

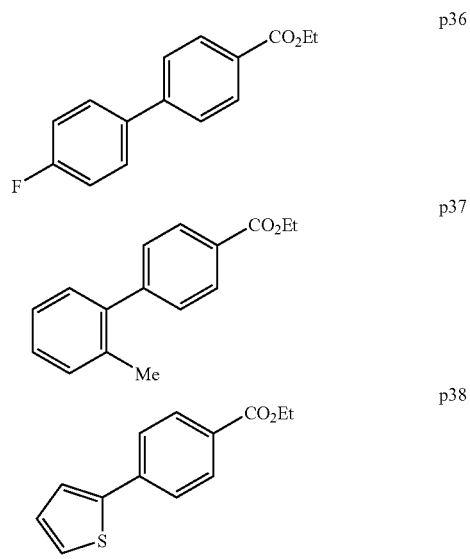

4'-fluorobiphenyl-4-carboxylic ethyl: 36

A colorless solid (mp 64.6-65.4° C.), $R_f$: 0.33 (hexane-ethyl acetate=10:1). $^1$H NMR (400 MHz, $CDCl_3$) δ 8.11 (d, J=8.5 Hz, 2H), 7.64-7.55 (m, 4H), 7.16 (t, J=8.8 Hz, 2H), 4.40 (q, J=7.1 Hz, 2H), 1.42 (t, J=7.1 Hz, 3H); $^{13}$C NMR (101 MHz, $CDCl_3$) δ 166.4, 162.9 (d, J=247.7 Hz), 144.5, 136.2, 130.1, 129.2, 128.9 (d, J=8.4 Hz), 126.8, 115.8 (d, J=22.2 Hz), 61.0, 14.3; Anal. Calcd for $C_{15}H_{13}FO_2$; C, 73.76; H, 5.36. Found: C, 73.49; H, 5.34.

4-ethoxycarbonyl-2'-methylbiphenyl: p37

A colorless oil, $R_f$: 0.19 (hexane-ethyl acetate=20:1). $^1$H NMR (400 MHz, $CDCl_3$) δ 8.10 (d, J=8.3 Hz, 2H), 7.40 (d, J=8.3 Hz, 2H), 7.31-7.21 (m, 4H), 4.41 (q, J=7.1 Hz, 2H), 2.27 (s, 3H), 1.42 (t, J=7.1 Hz, 3H); $^{13}$C NMR (101 MHz, $CDCl_3$) δ 166.6, 146.6, 140.9, 135.2, 130.5, 129.5, 129.4, 129.2, 128.9, 127.8, 125.9, 61.0, 20.4, 14.4; Anal. Calcd for $C_{16}H_{16}O_2$; C, 79.97; H, 6.71. Found: C, 79.83; H, 6.76.

2-(4-ethoxycarbonylphenyl)thiophene: p38

A colorless solid (mp 66.3-67.3° C.), $R_f$: 0.36 (hexane-ethyl acetate=10:1). $^1$H NMR (400 MHz, $CDCl_3$) δ 8.05 (d, J=8.6 Hz, 2H), 7.67 (d, J=8.6 Hz, 2H), 7.42 (d, J=3.7 Hz, 1H), 7.36 (d, J=5.1 Hz, 1H), 7.12 (dd, J=5.1, 3.7 Hz, 1H), 4.39 (q, J=7.1 Hz, 2H), 1.41 (t, J=7.1 Hz, 3H); $^{13}$C NMR (101 MHz, $CDCl_3$) δ 166.3, 143.1, 138.5, 130.2, 129.1, 128.3, 126.2, 125.5, 124.4, 61.0, 14.3; Anal. Calcd for $C_{13}H_{12}O_2S$; C, 67.21; H, 5.21. Found: C, 67.01; H, 5.25.

Example 6

Method for Preparing Organic Compounds by Using the Silicon-Based Cross-Coupling Reagent 2a of the Present Invention As expressed by the following reaction formula (Iv), the silicon-based cross-coupling reagent 2a of the present invention was used to prepare various organic compounds by carrying out a cross-coupling reaction between the silicon-based cross-coupling reagent 2a and an organic halide Br—$R^{10}$. Each of Table 3 and Table 4 shows the organic halide Br—$R^{10}$, amounts (mmol) of the silicon-based cross-coupling reagent 2a used, reaction times (h), yields of the resultant $R^1$-$R^{10}$, and yields of oxasilacyclopentane ((11') in the reaction formula (Iv)) generated as a by product.

TABLE 3

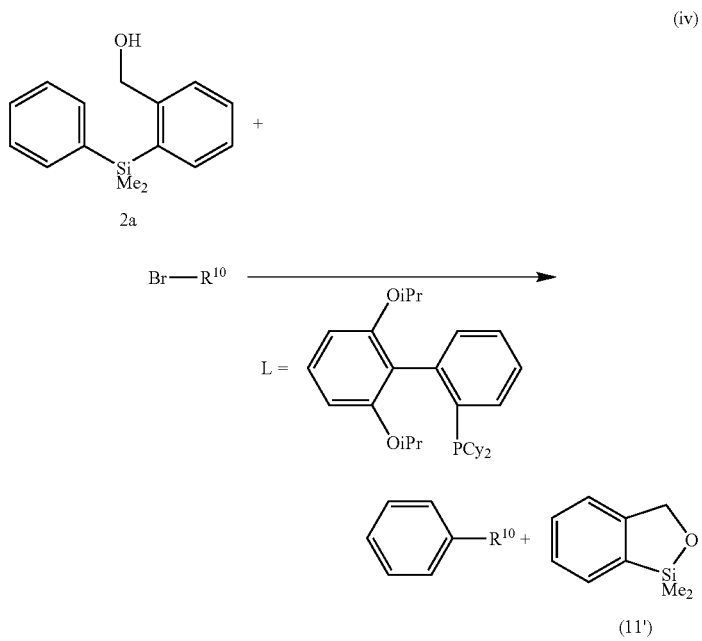

| Product | Br—$R^{10}$ | 2a (mmol) | Reaction time (h) | Yield (%) of $R^1$—$R^{10}$ | Yield (%) of Cyclic silyl ether |
|---|---|---|---|---|---|
| P51 | Br—⟨⟩—$CF_3$ | 1.3 | 12 | 86 | 91 |
| P52 | Br—⟨⟩—CN | 1.2 | 9 | 92 | 81 |
| P53 | Br—⟨⟩—Ac | 1.5 | 26 | 87 | 88 |
| P54 | Br—⟨⟩—$CO_2Et$ | 1.2 | 10 | 81 | 79 |
| P55 | Br—⟨⟩—CHO | 1.2 | 9 | 91 | 82 |
| P56 | Br—⟨⟩—$NO_2$ | 1.5 | 26 | 97 | 70 |

TABLE 3-continued
(iv)
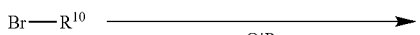
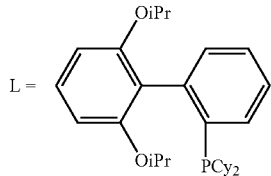
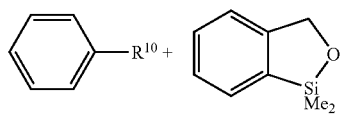
(11')
| Product | Br—R$^{10}$ | 2a (mmol) | Reaction time (h) | Yield (%) of R$^1$—R$^{10}$ | Yield (%) of Cyclic silyl ether |
|---|---|---|---|---|---|
| P57 | Br—C$_6$H$_4$—NO$_2$ (o) | 1.2 | 7 | 80 | 73 |
| P58 | Br—C$_6$H$_4$—F | 1.2 | 25 | 85 | 76 |
| P59 | Br—C$_6$H$_4$—Cl | 1.5 | 26 | 85 | 76 |
| P60 | Br—C$_6$H$_4$—Me | 1.3 | 19 | 86 | 71 |
| P61 | Br—C$_6$H$_4$—t-Bu | 1.3 | 56 | 82 | 46 |
| P62 | Br—C$_6$H$_4$—OMe | 1.5 | 23 | 91 | 72 |
| P63 | Br—C$_6$H$_4$—NH$_2$ (m) | 1.3 | 25 | 95 | 74 |

TABLE 4

| Product | Br—R$^{10}$ | 2a (mmol) | Reaction time (h) | Yield (%) of R$^1$—R$^{10}$ | Yield (%) of cyclic silyl ether |
|---|---|---|---|---|---|
| P64 | Br—[benzodioxole] | 1.3 | 27 | 88 | 91 |
| P65 | Br—[C6H4]—CH2OH | 1.2 | 24 | 92 | 68 |
| P66 | Br—[naphthyl] | 1.3 | 22 | 88 | >95 |
| P67 | [2-bromothiophene] | 1.3 | 11 | 90 | 88 |
| P68 | Br—[benzothiophene] | 1.2 | 22 | 83 | 70 |
| P69 | Br—[quinoline] | 1.2 | 27 | 97 | 88 |
| P70 | Br—[indole-NBoc] | 1.2 | 46 | 83 | 40 |

In the present Example, a mixture of DMF (0.8 mL) and THF (2.2 mL) was used as a solvent. The organic halide Br—R$^{10}$ (1.0 mmol) was sequentially added to a mixture of the silicon-based cross-coupling reagent 2a, K$_2$CO$_3$ (2.5 mmol), [($\eta^3$-C$_3$H$_5$)PdCl]$_2$ (0.5 mol % with respect to the organic halide), 2-(dicyclohexylphosphino)-2',6'-isopropoxybiphenyl (ligand L: 2.1 mol % with respect to the organic halide), CuI (3 mol % with respect to the organic halide) in the solvent, and the resulting mixture was stirred at 75° C. When each time period shown in Tables 3 and 4 had passed, the resulting mixture was diluted with diethyl ether and was washed with water and brine, and then was dried over anhydrous MgSO$_4$. After concentration with an evaporator, the residue was purified by flash chromatography on silica gel, thereby obtaining organic compounds p51 to p70 which were cross-coupling products respectively corresponding to yields shown in Tables 3 and 4.

Example 7

Method for Preparing an Organic Compound by Using the Silicon-Based Cross-Coupling Reagent 2a of the Present Invention As expressed by the following reaction formula (v), the silicon-based cross-coupling reagent 2a of the present invention was used to produce an organic compound p71 by carrying out a cross-coupling reaction between the silicon-based cross-coupling reagent 2a and an organic halide 4-(4,4,5,5-tetramethyl-1,3,2-dioxaborolane-2-yl)bromobenzene (v1).

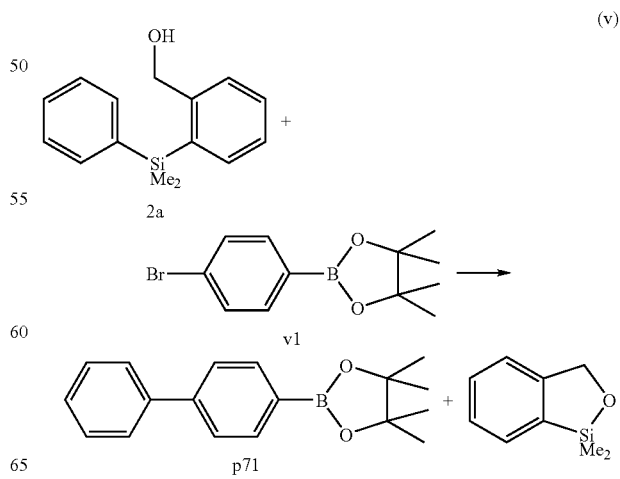

In the present Example, first, BuLi (1.1 mol with respect to 1 mol of the silicon-based cross-coupling reagent 2a) was added to the silicon-based cross-coupling reagent 2a (1.5 mmol) in THF (1.1 mL) at −78° C., and the mixture was stirred, and the reaction solution was warmed gradually at room temperature. In this manner, lithium salt was made from the silicon-based cross-coupling reagent 2a.

Next, DMF (0.4 mL) was added to the reaction solution, and a mixture of DMF and THF was used as a solvent. 4-(4,4,5,5-tetramethyl-1,3,2-dioxaborolane-2-yl)bromobenzene (v1) (1.0 mmol) was added to a mixture of lithium salt of the silicon-based cross-coupling reagent 2a, [($\eta^3$-allyl)PdCl]$_2$ (1.5 mol % with respect to the organic halide), ligand as in Example 6 (6.3 mol % with respect to the organic halide), and CuI (3.0 mol % with respect to the organic halide) in the solvent, and the resulting mixture was stirred at 75° C. for 11 hours. The mixture was diluted with diethyl ether, and the resultant was washed with brine and then was dried over anhydrous MgSO$_4$. After concentration with an evaporator, the residue was purified by flash chromatography on silica gel, thereby obtaining an organic compound p71 (yield of 81%).

Example 8

Gram-Scale Cross-Coupling Reaction

In the present Example, a mixture of DMF and THF (DMF THF (volume ratio)=1:2) was used as a solvent. The silicon-based cross-coupling reagent 2a (26 mmol) and 3-bromotoluene (20 mmol) was added to a mixture of K$_2$CO$_3$ (50 mmol), [($\eta^3$-allyl)PdCl]$_2$ (0.5 mol % with respect to 3-bromotoluene), ligand as in Example 6 (2.0 mol % with respect to 3-bromotoluene), and CuI (3.0 mol % with respect to 3-bromotoluene) in THF and DMF (30 mL), and the resulting mixture was stirred at 75° C. for 14 hours. The mixture was diluted with diethyl ether and was washed with water and brine, and then was dried over anhydrous MgSO$_4$. After concentration with an evaporator, the concentrated resultant was distilled under reduced pressure (1.0 mmHg), thereby obtaining cyclic silyl ether whose purity was about 90% (corresponding to the aforementioned formula (11)) (yield of 91%). The residue thereof was further purified by flash chromatography on silica gel, thereby obtaining 3-methylbiphenyl (yield of 87%).

The cyclic silyl ether (corresponding to the aforementioned formula (11)) obtained as a by product was treated with phenylmagnesium bromide in THF-ethanol mixture solvent at −78° C., and the resultant was warmed at room temperature, thereby reproducing the silicon-based cross-coupling reagent 1a (yield of 95%).

Example 9

Method for Preparing Organic Compounds by Using The Silicon-Based Cross-Coupling Reagent 2e of the Present Invention The silicon-based cross-coupling reagent 2e of the present invention was used to produce various organic compounds by carrying out a cross-coupling reaction between the silicon-based cross-coupling reagent 2e and an organic halide X—R$^{10}$. The reaction formula is as follows. Table 5 shows the organic halide X—R$^{10}$, amounts (mmol) of the silicon-based cross-coupling reagent 2e used, reaction times (h), yields of the resultants R$^1$-R$^{10}$, and yields of cyclic silyl ether ((11″) in the reaction formula (iv)) generated as a by product.

TABLE 5

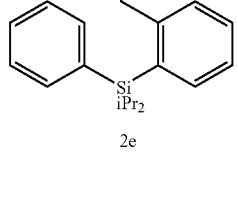

| Product | X—R$^{10}$ | 2e (mmol) | Reaction time (h) | R$^1$—R$^{10}$ Yield (%) | Yield (%) of cyclic silyl ether |
|---|---|---|---|---|---|
| P81 | Br—⟨⟩—t-Bu | 1.3 | 21 | 94 | >95 |
| P82 | Br—⟨⟩—OTBS | 1.2 | 16 | 86 | >95 |

TABLE 5-continued (vi)

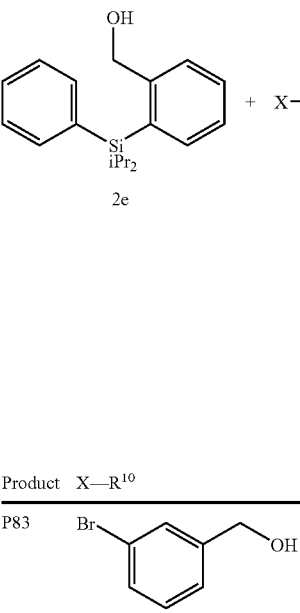

| Product | X—R¹⁰ | 2e (mmol) | Reaction time (h) | R¹—R¹⁰ Yield (%) | Yield (%) of cyclic silyl ether |
|---|---|---|---|---|---|
| P83 | 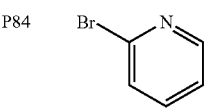 | 1.3 | 21 | 90 | >95 |
| P84 | 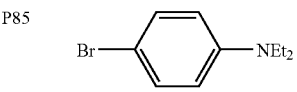 | 1.3 | 23 | 95 | >95 |
| P85 | 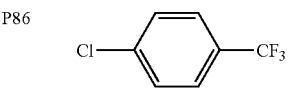 | 1.5 | 11 | 60 | >95 |
| P86 | 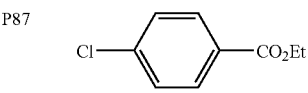 | 1.3 | 20 | 89 | 92 |
| P87 |  | 1.5 | 15 | 99 | >95 |

In the present Example, a mixture of DMF (0.8 mL) and THF mL) was used as a solvent. The organic halide X—R¹⁰ (1.0 mmol) was added to a mixture of the silicon-based cross-coupling reagent 2e, $K_2CO_3$ (2.5 mmol), $[(\eta^3\text{-}C_3H_5)PdCl]_2$ mol % with respect to the organic halide), ligand as in Example 6 (2.1 mol % with respect to the organic halide), and CuI (3 mol % with respect to the organic halide) in the solvent, and the resulting mixture was stirred at 75° C. for the time specified in Table 5. The resulting mixture was diluted with diethyl ether and was washed with water and brine, and then was dried on anhydrous $MgSO_4$. After concentration with an evaporator, the residue was purified by flash chromatography on silica gel, thereby obtaining organic compounds p81 to p87 which were cross-coupling products respectively corresponding to yields shown in Table 5.

INDUSTRIAL APPLICABILITY

By using the silicon-based cross-coupling reagent according to the present invention, it is possible to carry out a cross-coupling reaction, which allows formation of an sp²-sp² carbon bond or an sp²-sp carbon bond between desired organic groups, under mild conditions, and it is possible to realize extremely high stability of the silicon-based cross-coupling reagent. Therefore, it is possible to carry out a cross-coupling reaction so efficiently and it is possible to obtain an organic compound which is a cross-coupling product in a high yield. In this way, the present invention is so useful. Further, the silicon-based cross-coupling reagent of the present invention is superior to a boron-based cross-coupling reagent in view of reusability and cost.

Thus, the silicon-based cross-coupling reagent is expected to be applied to a great variety of organic compounds, particularly, to construction of a π-conjugated system serving as a key compound of a pharmaceutical agent, a liquid crystal material, or a molecular-scale electronics element. Therefore, the present invention is usable and so useful in various kinds of chemical industries such as medical drug production, industrial chemical production, industrial material production, and the like, further, in pharmaceutical industry, electronics industry, and the like.

The invention claimed is:

1. A silicon-based cross-coupling reagent, comprising:
an organosilicon compound reacting with an organic compound having a halogen leaving group or a pseudo halogen leaving group in the presence of a palladium catalyst and a base to form a carbon-carbon bond between a carbon atom connected to the halogen leaving group or the pseudo halogen leaving group and a carbon atom connected to a silicon atom of the organosilicon compound in accordance with a cross-coupling reaction,
wherein the silicon-based cross-coupling reagent has a structure represented by the following formula (1)
where $R^1$ represents a linear, branched, or cyclic hydrocarbon group having a substituent or no substituent or a heterocyclic group having a substituent or no substituent, and each of $R^2$ and $R^3$ represents an alkyl group in an independent manner, and each of $R^4$, $R^5$, $R^{61}$, $R^{62}$, $R^{63}$, and $R^{64}$ represents a hydrogen atom or an alkyl group in an independent manner,
the substituent being a hydrocarbon group, heterocyclic group, cyano group, formyl group, alkoxycarbonyl group, carboxyl group, phosphate group, sulfo group, hydroxy group, sulfonyl group, halogen, acyl group, alkoxy group, amino group, nitro group, imino group, trialkylsiloxy group, or hydroxyl alkyl group, and
$R^1$ having at least one double bond, and an $sp^2$ carbon atom of $R^1$ is connected to a silicon atom.

2. The silicon-based cross-coupling reagent as set forth in claim 1, wherein the silicon-based cross-coupling reagent has a structure represented by the following formula (2)

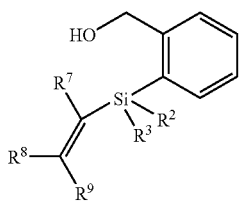

(2)

where each of $R^2$ and $R^3$ represents in an independent manner a linear or branched alkyl group whose carbon number is 1 to 6, and each of $R^7$, $R^8$, and $R^9$ represents in an independent manner a hydrogen atom, a linear or branched alkyl group which has or does not have a substituent and whose carbon number is 1 to 10, or an aryl group whose carbon number is 6 to 10,
the substituent being a hydrocarbon group, heterocyclic group, cyano group, formyl group, alkoxycarbonyl group, carboxyl group, phosphate group, sulfo group, hydroxy group, sulfonyl group, halogen, acyl group, alkoxy group, amino group, nitro group, imino group, trialkylsiloxy group, or hydroxyl alkyl group.

3. The silicon-based cross-coupling reagent as set forth in claim 1, wherein $R^1$ represents an aryl group which has or does not have a substituent and whose carbon number is 6 to 10 or a heterocyclic group which has or does not have a substituent,
the substituent being a hydrocarbon group, heterocyclic group, cyano group, formyl group, alkoxycarbonyl group, carboxyl group, phosphate group, sulfo group, hydroxyl group, sulfonyl group, halogen, acyl group, alkoxy group, amino group, nitro group, imino group, trialkylsiloxy group, or hydroxy alkyl group.

4. A compound, having a structure represented by any one of the following chemical formulas 1a, 1b, 1c, 1d, 1e, 1f, 1g, 1h, 1i, 2a, 2b, 2c, 2d, and 2e.

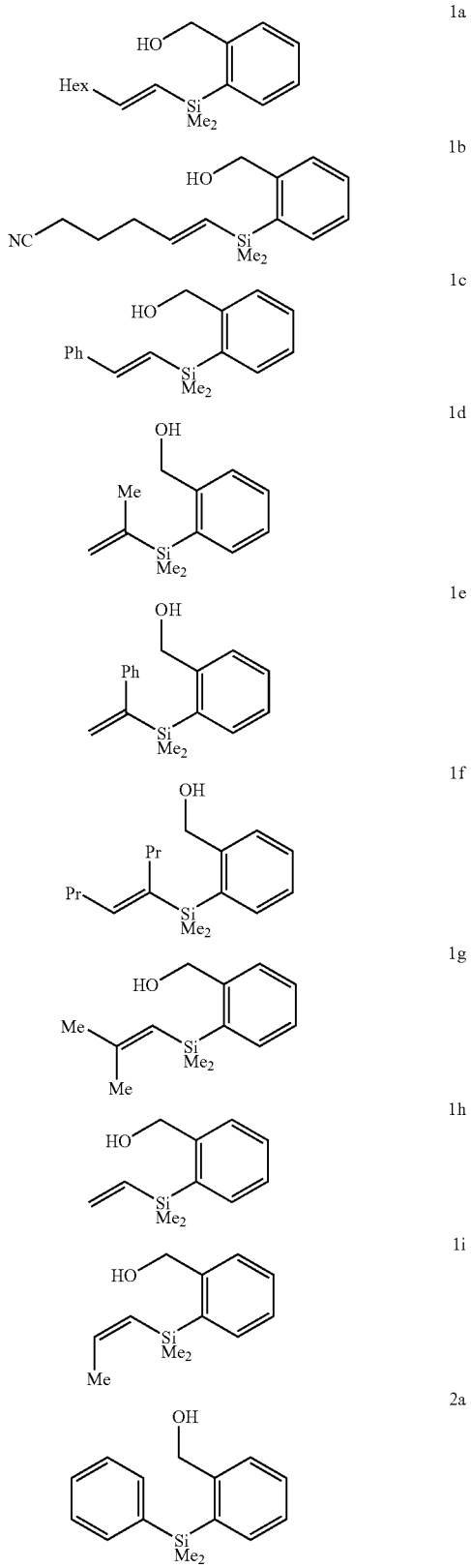

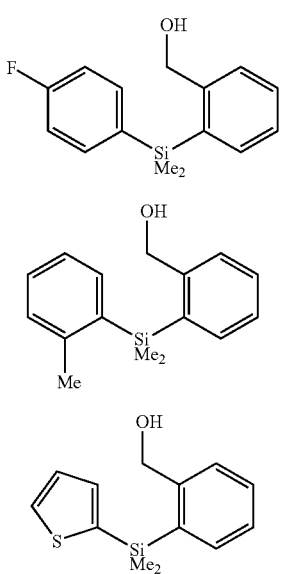

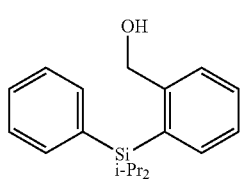

5. A method for producing an organic compound, comprising a cross-coupling step in which a cross-coupling reaction between the silicon-based cross-coupling reagent as set forth in claim 1 and an organic compound having a halogen leaving group or a pseudo halogen group is carried out in the presence of a palladium catalyst and a base.

6. The method as set forth in claim 5, further comprising an isolation step in which a residue of the silicon-based cross-coupling reagent is recovered.

* * * * *